(12) United States Patent
Aouidate et al.

(10) Patent No.: US 7,384,935 B2
(45) Date of Patent: *Jun. 10, 2008

(54) PHOSPHATE PRODRUGS OF A FARNESYL DIBENZODIAZEPINONE, PROCESSES FOR THEIR PRODUCTION AND THEIR USE AS PHARMACEUTICALS

(75) Inventors: Mustapha Aouidate, Saint-Laurent (CA); James B. McAlpine, Montreal (CA); Faustinus Yeboah, Longueuil (CA); Ashraf Ibrahim, Kirkland (CA); Arjun H. Banskota, Saint-Laurent (CA); Maxime Ranger, Montreal (CA); Gregory L. White, Ile-Perrot (CA)

(73) Assignee: Thallion Pharmaceuticals, Inc., Montreal (CA)

( * ) Notice: Subject to any disclaimer, the term of this patent is extended or adjusted under 35 U.S.C. 154(b) by 0 days.

This patent is subject to a terminal disclaimer.

(21) Appl. No.: 11/527,581

(22) Filed: Sep. 27, 2006

(65) Prior Publication Data

US 2007/0078112 A1   Apr. 5, 2007

Related U.S. Application Data

(63) Continuation-in-part of application No. 11/253,658, filed on Oct. 20, 2005, which is a continuation-in-part of application No. 11/235,398, filed on Sep. 27, 2005, now Pat. No. 7,304,054.

(51) Int. Cl.
   *C07D 243/10*   (2006.01)
   *A61K 31/551*   (2006.01)
   *A61P 35/00*    (2006.01)

(52) U.S. Cl. ..................... 514/220; 540/495

(58) Field of Classification Search ................ 540/495; 514/220

See application file for complete search history.

(56) References Cited

U.S. PATENT DOCUMENTS 6,423,753 B1   7/2002   Dougherty
2006/0276436 A1*  12/2006   Ranger et al. ............... 514/80

OTHER PUBLICATIONS

Search Report and Written Opinion for International Application No. PCT/US06/37490, mail date Sep. 11, 2007.

* cited by examiner

*Primary Examiner*—Bruck Kifle

(57) ABSTRACT

This invention relates to phosphate prodrugs of a farnesylated dibenzodiazepinone, to processes of their manufacture, to pharmaceutical compositions comprising the prodrugs, and to their use in the treatment of neoplasms.

22 Claims, 6 Drawing Sheets

PHOSPHATE PRODRUGS OF A FARNESYL DIBENZODIAZEPINONE, PROCESSES FOR THEIR PRODUCTION AND THEIR USE AS PHARMACEUTICALS

RELATED APPLICATIONS

This application is a continuation-in-part of U.S. application Ser. No. 11/253,658, filed Oct. 20, 2005, which is a continuation-in-part of U.S. application Ser. No. 11/235,398, filed Sep. 27, 2005 now U.S. Pat. No. 7,304,054. The entire teachings of the above applications are incorporated herein by reference.

FIELD OF THE INVENTION

This invention relates to prodrugs of a farnesyl dibenzodiazepinone, represented as prodrugs of the naturally produced farnesylated dibenzodiazepinone referred to herein as Compound 1, and their pharmaceutically acceptable salts and solvates, and to methods for obtaining and using the compounds. One method of obtaining the prodrugs involves post-biosynthesis chemical modification of Compound 1. More specifically, the invention relates to phosphate prodrugs of parent Compound 1, and their pharmaceutically acceptable salts and solvates, and their use as pharmaceuticals in the inhibition of cancer cell growth and/or specific disease pathways, and to pharmaceutical compositions comprising a dibenzodiazepinone analogue, or a pharmaceutically acceptable salt, solvate or prodrug thereof.

BACKGROUND OF THE INVENTION

The farnesyl dibenzodiazepinone Compound 1 was isolated from *Micromonospora* sp. strains 046-ECO11and [S01]046, and was disclosed in U.S. Patent Application publication No. 2005/0043297, incorporated by reference in its entirety. Compound 1 was also disclosed in Charan et al. (2004), *J. Nat. Prod.*, vol 67, 1431-1433, and Igarashi et al. (2005), *J. Antibiot.*, vol 58, no 5, 350-352. Its use for the treatment of cancer is disclosed in US patent publication numbers 2005/0107363 and 2006/0079508, both incorporated herein by reference in their entirety.

Compound 1

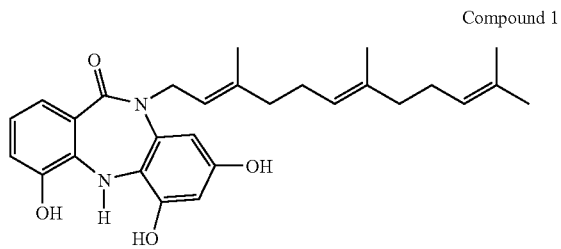

Compound 1 was further shown to exhibit antibacterial activity, as well as binding or inhibitory activity against 5-lipoxygenase (5-LO), acyl CoA-cholesterol acyltransferase (ACAT), cyclooxygenase-2 (COX-2), the peripheral benzodiazepine receptor (PBR), and leukotriene cysteinyl ($CysLT_1$) in US patent publication No. 2006/0079508, US Patent Application publication No. 2005/0043297 and in Canadian patent application 2,511,750, filed Jul. 21, 2005, all incorporated by reference in their entirety for all purposes. Most recently, Compound 1 was shown to be involved in the inhibition of the binding of ras-F to galectin (Gourdeau et al, Poster presented at 12$^{th}$ Meeting on Protein Phosphorylation and Cell Signaling, Salk Institute, La Jolla, Calif. Aug. 18-22, 2006).

Phosphate prodrugs have been produced for anticancer drugs, including ZD-6126 (N-acetylcolchinol-O-Phosphate, U.S. Pat. No. 6,423,753, issued to Dougherty) and Combretastatin A4 phosphate (U.S. Pat. No. 5,561,122, issued to Pettit) and A1 diphosphate (U.S. Pat. No. 7,078,552, issued to Pettit et al), all incorporated by reference in their entirety.

The farnesyl dibenzodiazepinone Compound 1 is highly lipophilic and is nearly insoluble in aqueous media. Formulation of Compound 1 thus often requires the use of solubilizers having some toxicity level, e.g. Cremophor EL™, poly(ethylene glycol)s or polysorbates. There is a need for a precursor of Compound 1 with improved chemical and biological properties, such as solubility and bioavailability. A highly desirable precursor would be a prodrug of Compound 1 stable enough to be formulated and administered, and which would release the active drug in vivo.

SUMMARY OF THE INVENTION

The present invention relates to the following compounds: (a) phosphate prodrugs of the farnesyl dibenzodiazepinone Compound 1, and (b) pharmaceutically acceptable salts or solvates thereof, and further relates to pharmaceutical compositions comprising these compounds, together with a pharmaceutically acceptable carrier.

Compound 1

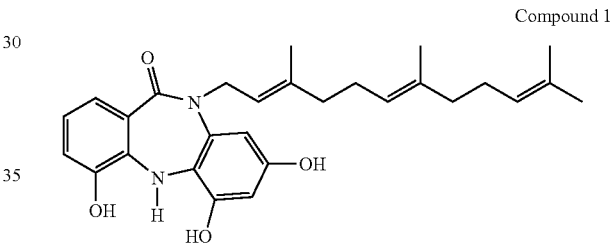

In one embodiment, the compounds of the present invention include the compounds of Formula I:

Formula I

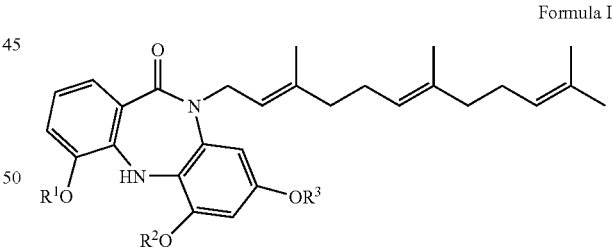

wherein, $R^1$ $R^2$ and $R^3$ are each independently selected from the group consisting of H and a phosphate of formula II:

formula II

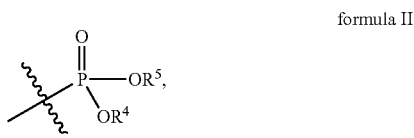

wherein at least one of $R^1$, $R^2$, or $R^3$ is a phosphate of formula II;

$R^4$ and $R^5$ are each independently selected from the group consisting of H, $C_{1-10}$alkyl, $C_{2-10}$alkenyl, $C_{2-10}$alkynyl, $C_{6-10}$aryl, $C_{5-10}$heteroaryl, $C_{3-10}$cycloalkyl, and $C_{3-10}$heterocycloalkyl;

wherein, when either or both of $R^4$ and $R^5$ comprises an alkyl, alkenyl, alkynyl, aryl, heteroaryl, cycloalkyl, or heterocycloalkyl group, then the alkyl, alkenyl, alkynyl, aryl, heteroaryl, cycloalkyl, or heterocycloalkyl group is optionally substituted with one or more substituents selected from the group consisting of acyl, amino, acylamino, acyloxy, carboalkoxy, carboxy, carboxyamido, cyano, halo, hydroxyl, nitro, $C_{1-6}$alkyl, $C_{2-7}$alkenyl, $C_{2-7}$alynkyl, $C_{3-10}$cycloalkyl, C31heterocycloalkyl, $C_{6-10}$aryl, $C_{5-10}$heteroaryl, alkoxy, aryloxy, sulfinyl, sulfonyl, oxo, guanidino and formyl;

and to pharmaceutically acceptable salts and solvates thereof.

In an equally preferred embodiment, the compounds of the present invention include compounds of Formula I:

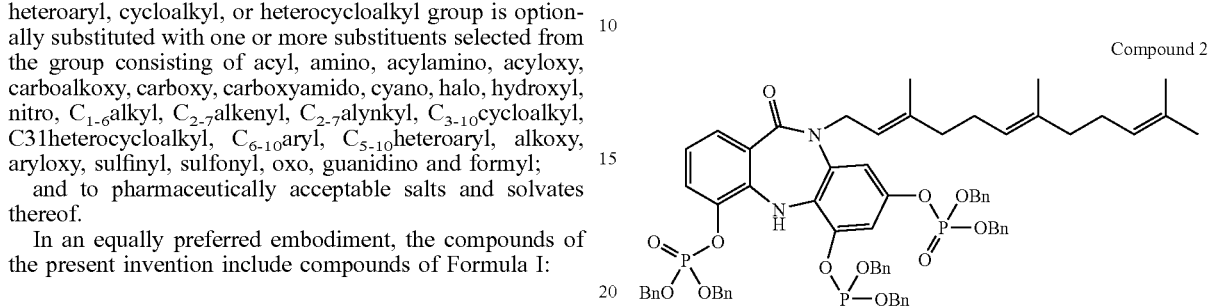

Formula I wherein, $R^1$ $R^2$ and $R^3$ are each independently selected from the group consisting of H and a phosphate of formula II:

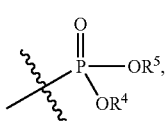

formula II wherein at least one of $R^1$, $R^2$, or $R^3$ is a phosphate of formula II;

$R^4$ and $R^5$ are each independently selected from the group consisting of H, $C_{1-10}$alkyl, $C_{2-10}$alkenyl, $C_{2-10}$alkynyl, $C_{6-10}$aryl, $C_{5-10}$heteroaryl, $C_{3-10}$cycloalkyl, and $C_{3-10}$heterocycloalkyl;

wherein at least one of $R^4$ and $R^5$ is H in at least one phosphate of formula II;

wherein, when either or both of $R^4$ and $R^5$ comprises an alkyl, alkenyl, alkynyl, aryl, heteroaryl, cycloalkyl, or heterocycloalkyl group, then the alkyl, alkenyl, alkynyl, aryl, heteroaryl, cycloalkyl, or heterocycloalkyl group is optionally substituted with one or more substituents selected from the group consisting of acyl, amino, acylamino, acyloxy, carboalkoxy, carboxy, carboxyamido, cyano, halo, hydroxyl, nitro, $C_{1-6}$alkyl, $C_{2-7}$alkenyl, $C_{2-7}$alkynyl, $C_{3-10}$cycloalkyl, $C_{3-10}$heterocycloalkyl, $C_{6-10}$aryl, $C_{5-10}$heteroaryl, alkoxy, aryloxy, sulfinyl, sulfonyl, oxo, guanidino and formyl;

and to pharmaceutically acceptable salts and solvates thereof.

In preferred embodiments, the compounds of the present invention are compounds of Formula I wherein $R^1$ is H, wherein $R^2$ is H, wherein $R^3$ is H, wherein $R^1$ and $R^2$ are each H, wherein $R^1$ and $R^3$ are each H, wherein $R^2$ and $R^3$ are each H, or wherein $R^1$, $R^2$ and $R^3$ are each a phosphate of formula II, as well as pharmaceutically acceptable salts and solvates of these compounds.

In a further embodiment of the present invention, the compounds of the present invention include each of Compounds 2 to 22:

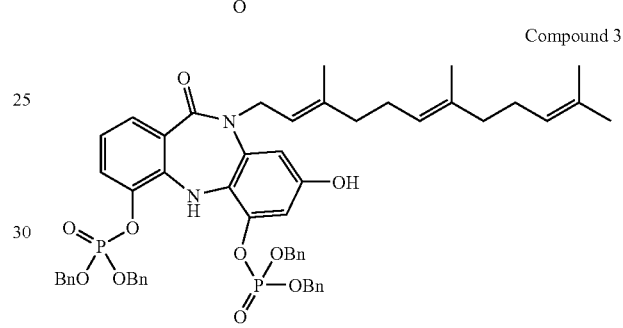

Compound 2

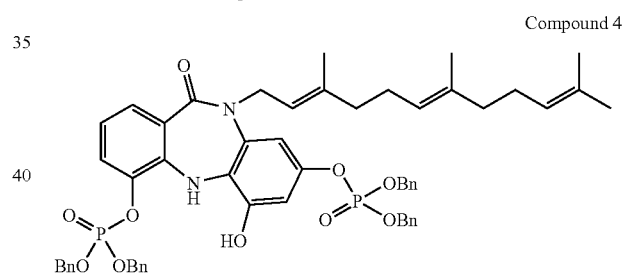

Compound 3

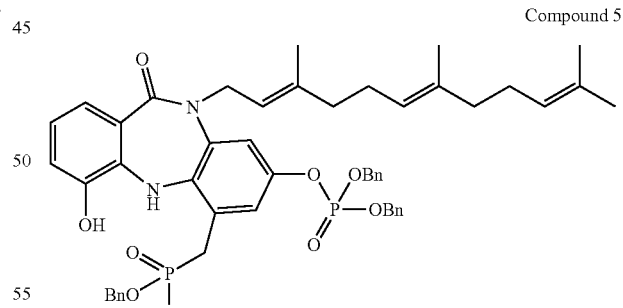

Compound 4

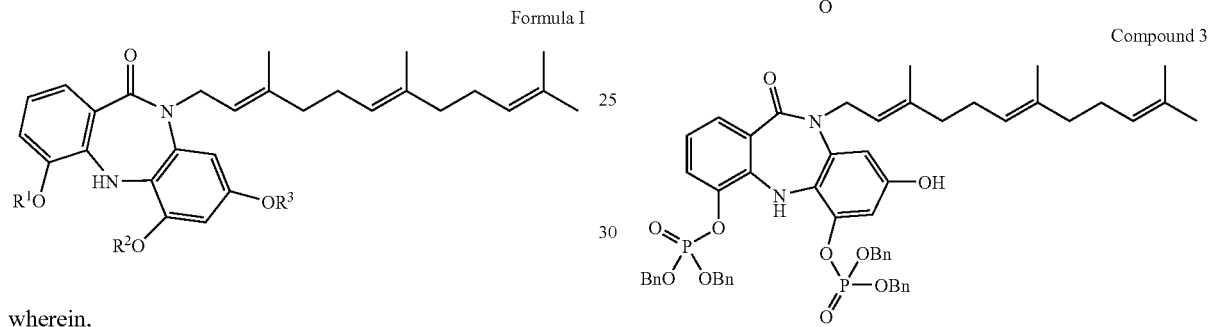

Compound 5

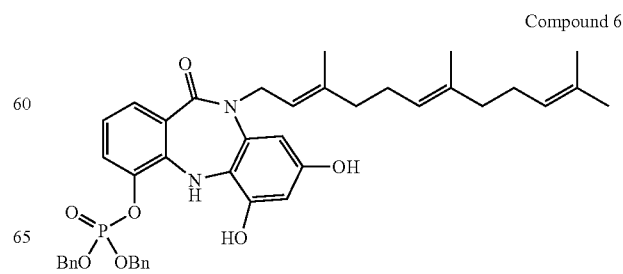

Compound 6

Compound 7
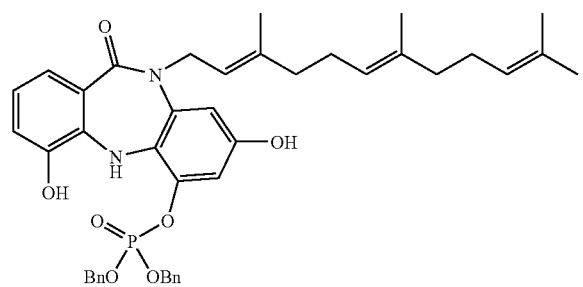
Compound 12
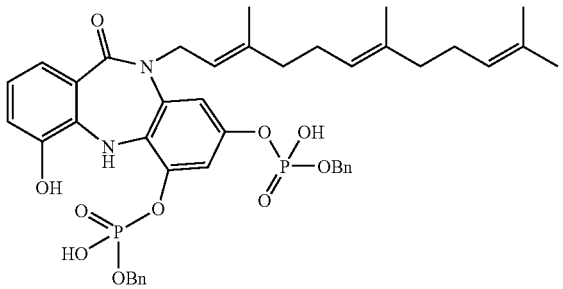
Compound 8
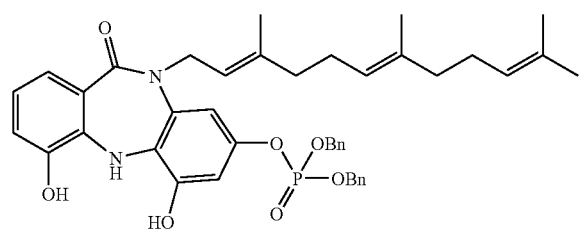
Compound 13
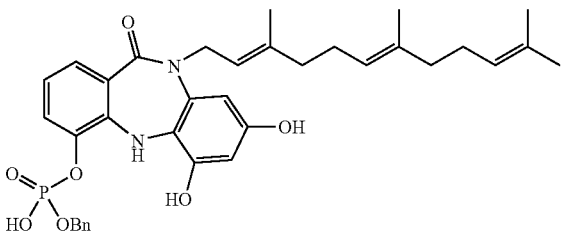
Compound 9
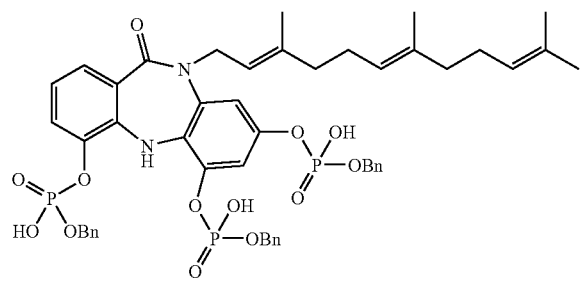
Compound 14
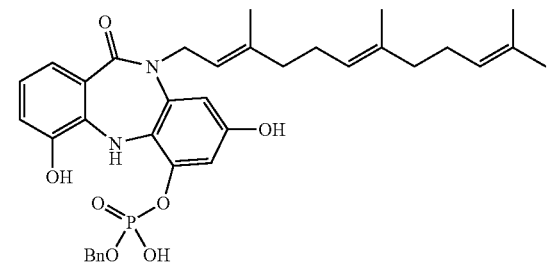
Compound 10
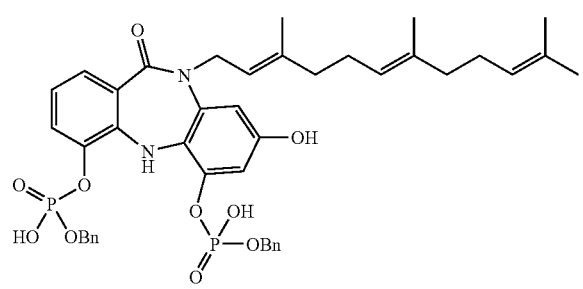
Compound 15
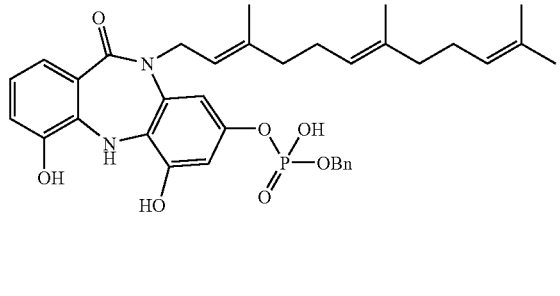
Compound 11
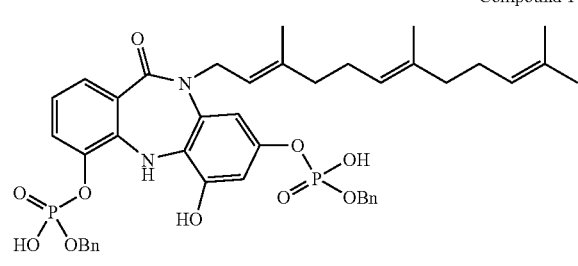
Compound 16
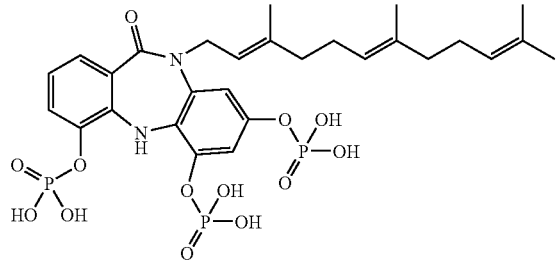

-continued

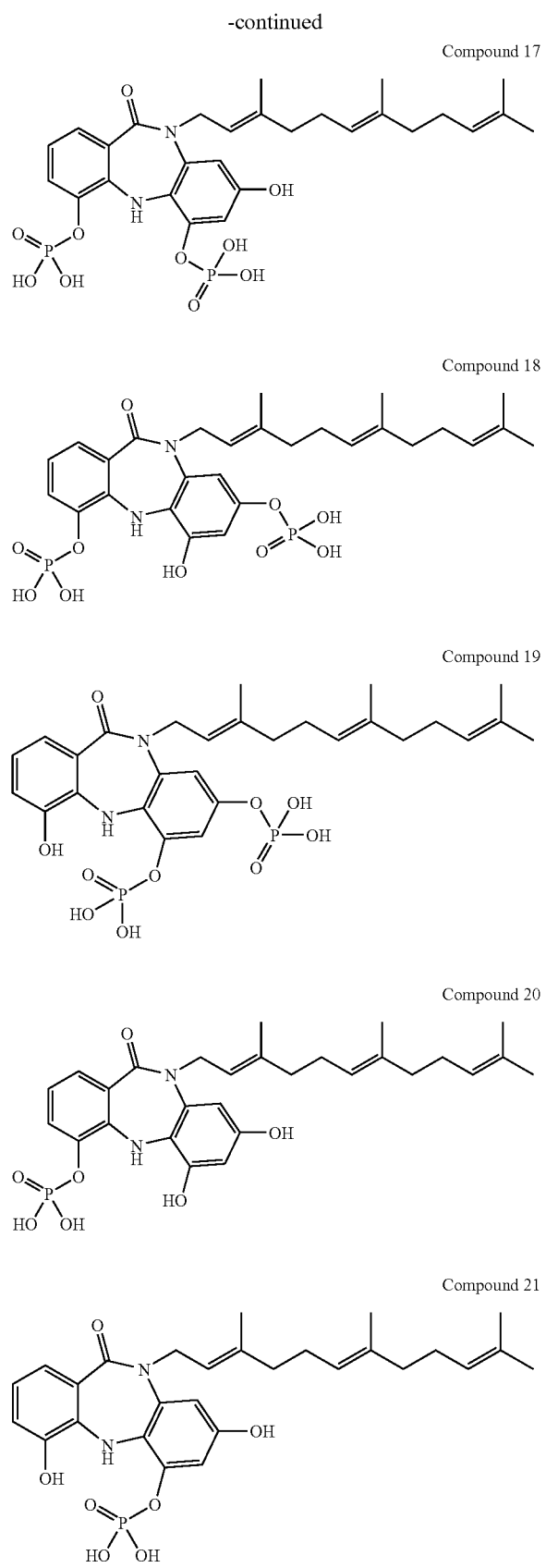

Compound 17

Compound 18

Compound 19

Compound 20

Compound 21

-continued

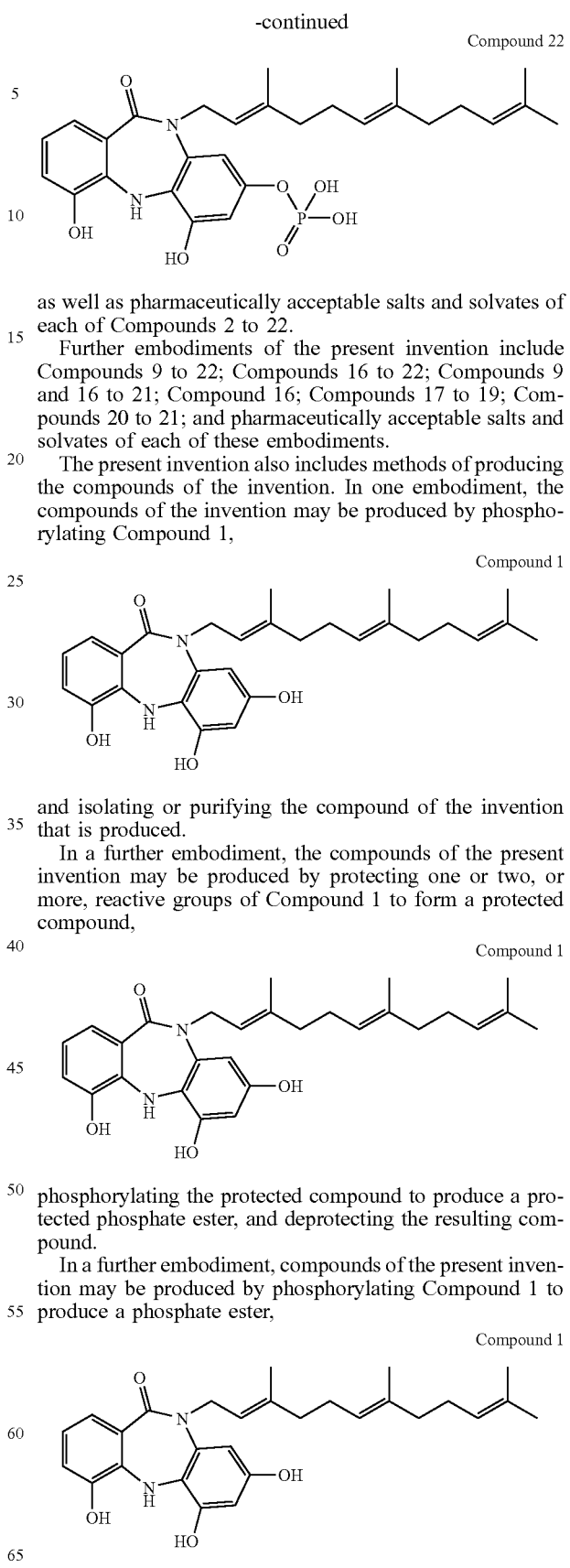

Compound 22 as well as pharmaceutically acceptable salts and solvates of each of Compounds 2 to 22.

Further embodiments of the present invention include Compounds 9 to 22; Compounds 16 to 22; Compounds 9 and 16 to 21; Compound 16; Compounds 17 to 19; Compounds 20 to 21; and pharmaceutically acceptable salts and solvates of each of these embodiments.

The present invention also includes methods of producing the compounds of the invention. In one embodiment, the compounds of the invention may be produced by phosphorylating Compound 1, Compound 1 and isolating or purifying the compound of the invention that is produced.

In a further embodiment, the compounds of the present invention may be produced by protecting one or two, or more, reactive groups of Compound 1 to form a protected compound, Compound 1 phosphorylating the protected compound to produce a protected phosphate ester, and deprotecting the resulting compound.

In a further embodiment, compounds of the present invention may be produced by phosphorylating Compound 1 to produce a phosphate ester, Compound 1 adding a base to the phosphate ester to remove a proton, thereby producing a salt of the phosphate ester, and isolating or purifying the salt of the phosphate ester.

The invention further encompasses a phosphate prodrug obtained by a method comprising one or more steps of chemically modifying Compound 1, comprising at least one phosphorylation step. In one embodiment the phosphate prodrug obtained by the method is a compound of Formula I or a pharmaceutically acceptable salt or solvate thereof. In a further embodiment, the phosphate prodrug obtained by the method is represented by any one of Compounds 2 to 22, or a pharmaceutically acceptable salt or solvate thereof.

The invention further encompasses a process for making a phosphate prodrug of Formula I, such as one or more of Compounds 2 to 22, or a pharmaceutically acceptable salt or solvate thereof, comprising the steps of (a) chemically modifying Compound 1; and (b) optionally isolating and purifying the phosphate prodrug produced. In one embodiment, step (a) comprises at least one phosphorylation step to produce a phosphate ester. In a subclass of this embodiment, step (a) further comprises deprotecting the phosphate ester to obtain a partially or fully deprotected phosphate, or a base addition salt thereof.

The invention further encompasses a method of inhibiting the growth of a cell, such as a neoplastic or cancer cell, by contacting a cell with a compound on the invention in an amount sufficient to inhibit growth of the cell. Such a method made be used in vitro, in vivo or ex vivo. In one embodiment, the cell is a cell of a neoplasm. In a preferred embodiment, the cell is a cell of a human. In another preferred embodiment, the method is performed in a subject, wherein the method comprises administering to a subject a compound of the invention, or a pharmaceutical composition comprising a compound of the invention, such that growth of a cancer cell is inhibited. In one embodiment, the subject is a mammal.

The invention further encompasses a method of treating a mammal having neoplastic, pre-cancerous or cancerous condition, comprising administering a therapeutically effective amount of a compound of the invention, or a pharmaceutical composition comprising a therapeutically effective amount of a compound of the invention, to the mammal, such that a neoplastic, pre-cancerous or cancerous condition is treated. In a preferred embodiment, the mammal is a human.

The invention further encompasses the use of a compound of the invention in the treatment of a neoplastic, pre-cancerous or cancerous condition in a mammal. The invention also further encompasses the use of a compound of the invention in the preparation of a medicament for the treatment of a neoplastic, pre-cancerous or cancerous condition.

The invention encompasses a commercial package or kit comprising a compound of the invention and instruction for the treatment of a neoplastic, as,c, pre-cancerous or cancerous condition.

The present invention also encompasses the use of a compound of the invention in the preparation of a medicament for use in the treatment of a neoplastic condition.

The neoplastic, pre-cancerous or cancerous conditions of the embodiments, therapeutic methods and uses described herein include leukemia, melanoma, breast cancer, lung cancer, pancreatic cancer, ovarian cancer, renal cancer, colon or colorectal cancer, prostate cancer, and CNS cancer. In particular embodiments, the neoplastic, pre-cancerous or cancerous condition is selected from leukemia, breast cancer, prostate cancer, and CNS cancer. The cancer cells of the embodiments, therapeutic methods and uses described herein include cells of leukemia, melanoma, breast cancer, lung cancer, pancreatic cancer, ovarian cancer, renal cancer, colon or colorectal cancer, prostate cancer, and CNS cancer. In particular embodiments, the cancer cells are cells of leukemia, breast cancer, prostate cancer, and CNS cancer.

The invention further encompasses methods and uses of a compound of the invention, or a pharmaceutical composition comprising a compound of the invention, in the treatment of bacterial infection, or for use as an inhibitor or binder of 5-lipoxygenase (5-LO), peripheral benzodiazepine receptor (PBR), acyl CoA-cholesterol acyltransferase (ACAT), cyclooxygenase-2 (COX-2), and leukotriene, cysteinyl ($CysLT_1$).

In a further aspect, the compound used in one or more of the above-mentioned therapeutic methods and uses, is a compound of Formula I, or a pharmaceutically acceptable salt or solvate thereof. In one embodiment, the compound is a compound selected from Compounds 2 to 22, or a pharmaceutically acceptable salt or solvate thereof.

DETAILED DESCRIPTION OF THE INVENTION

Figure 1:
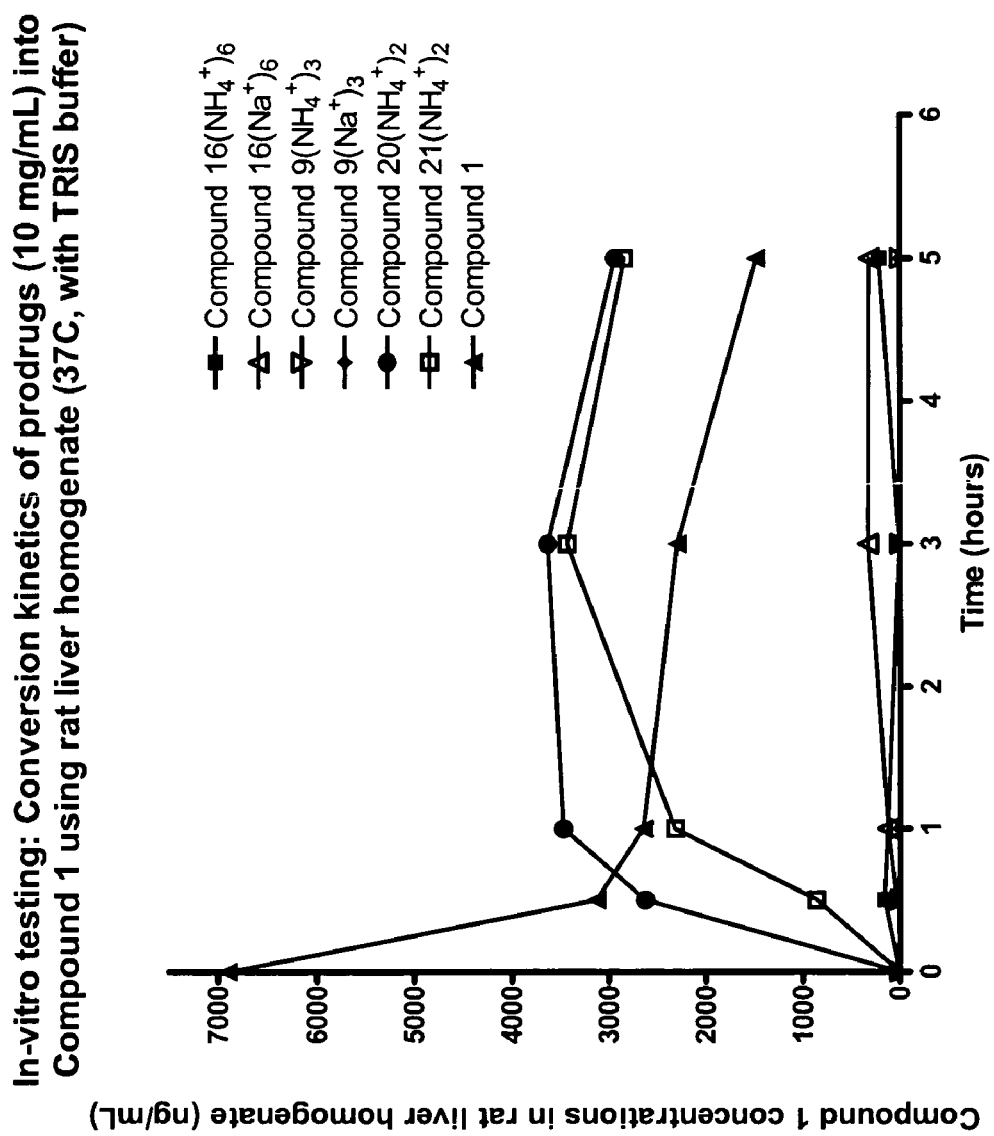
FIG. 1: shows levels of Compound 1 when Compounds 9-triammonium, 9-trisodium, 16-hexaammonium, 16-hexasodium, 20-diammonium and 21-diammonium are converted in vitro to Compound 1 using rat liver homogenate.

The present invention relates to novel dibenzodiazepinone prodrugs herein referred as the compounds of Formula I, and pharmaceutically acceptable salts and solvates thereof, which include phosphate prodrugs of parent Compound 1. In one embodiment, the novel dibenzodiazepinone prodrugs of the present invention are any one of the subgroups formed by Compounds 2 to 22, or Compounds 9 to 22, or Compounds 16 to 22.

The invention also relates to a method for producing novel dibenzodiazepinone prodrugs of Formula I, or a pharmaceutically acceptable salt or solvate thereof, by chemical modification of the farnesyl dibenzodiazepinone Compound 1. In one embodiment, the compound produced is a compound selected from Compounds 2 to 22, or Compounds 9 to 22 or Compounds 16 to 22, or a pharmaceutically acceptable salt or solvate of any one of the above compounds.

As the dibenzodiazepinone prodrugs of the invention are converted to Compound 1 in vivo, the dibenzodiazepinone prodrugs of the invention are useful as pharmaceuticals. The following detailed description discloses how to make and use the compounds of Formula I and compositions containing these compounds in the inhibition of tumor growth and/or inhibition of specific disease pathways, for example, in the inhibition and/or binding of 5-LO, PBR, ACAT, COX-2, $CysLT_1$, and inhibition of binding of ras-F to galectin.

Accordingly, certain aspects of the present invention relate to pharmaceutical compositions comprising the dibenzodiazepinone prodrugs of the present invention together with a pharmaceutically acceptable carrier, and methods of using the pharmaceutical compositions to treat diseases, including cancer, and chronic and acute inflammation, autoimmune diseases, and neurodegenerative diseases.

I. Definitions

All technical and scientific terms used herein have the same meaning as commonly understood by one of ordinary skill in the art to which this invention belongs. For convenience, the meaning of certain terms and phrases used in the specification, examples, and appended claims, are provided below.

As used herein, the term "farnesyl dibenzodiazepinone" refers to Compound 1, namely 10-farnesyl4,6,8-trihydroxy-5,10-dihydrodibenzo[b,e][1,4]diazepin-11-one.

As used herein, the terms "compound(s) of the invention", "dibenzodiazepinone prodrug(s)", "phosphate prodrug(s)", and equivalent expressions refer to a class of compounds derived from Compound 1 obtained by the replacement of a hydrogen atom from at least one alcohol, by a $P(O)(OR^4)(OR^5)$ phosphate group as defined below, and pharmaceutically acceptable salts and solvates thereof. The term includes a compound of Formula I, a compound selected from Compounds 2 to 22, a compound or a pharmaceutically acceptable salt or solvate of any one of the above compounds. As used herein, the term "dibenzodiazepinone prodrugs" and equivalents include compounds of this class that can be used as intermediates in chemical syntheses, and variants containing isotopes different than the most abundant isotope of an atom (e.g., D replacing H, $^{13}C$ replacing $^{12}C$, etc).

The term "prodrug" generally means any compound of this invention, which upon administration to a recipient, is capable of providing, either directly or indirectly, parent Compound 1 or a biologically active metabolite or residue thereof. Particularly favored prodrugs are those with improved properties, such as solubility, efficacy, or bioavailability of Compound 1 when such prodrugs are administered to a mammal (e.g., by allowing an orally administered compound to be more readily absorbed into the blood) or which enhance delivery of the parent compound to a biological compartment (e.g., the brain or lymphatic system) relative to the parent species. Generally, a prodrug is a drug having one or more functional groups covalently bound to a carrier wherein metabolic or chemical release of the drug occurs in vivo when the drug is administered to a mammalian subject. More particularly, the prodrug is a precursor that will undergo metabolic activation in vivo to the active drug. Certain phosphates make ideal prodrugs since they can be cleaved by endogenous non-specific phosphatases. For further examples of prodrugs used in anticancer therapy and their metabolism, see Rooseboom et al (2004), *Phamacol. Rev.*, vol 56, 53-102, incorporated herein by reference.

The term "active metabolite" as used herein generally means the active molecule obtained from the in vivo conversion of a prodrug. For example, the term "active metabolite" encompasses parent Compound 1 or a biologically active metabolite or residue thereof. In the context of calculating a dosage or therapeutically effective amount, for example, the amount of the prodrug would take into account the quantity of prodrug necessary to get the desired dose of the active metabolite. For example, 174 mg of Compound 16-hexaammonium (MW 804.31) would be equivalent to 100 mg of its active metabolite, Compound 1 (MW: 462.25).

As used herein, the term "chemical modification" refers to one or more steps of modifying a dibenzodiazepinone compound, referred to as "starting material", by chemical synthesis. Preferred compounds for use as starting materials in a chemical modification process are Compounds 1 to 22, more preferably Compound 1. Examples of chemical modification steps include phosphorylation, deprotection and salt formation. Chemical modification steps are also defined in the Scheme of Section III, and exemplified in Examples 2 to 4.

As used herein, abbreviations have their common meaning. Unless otherwise noted, the abbreviations "Ac", "Me", "Bz", "Bn", "SD", "i.v." and "i.p." respectively refer to acetyl, methyl, benzoyl, benzyl, standard deviation, intravenous and intraperitoneal. Abbreviations in the specification correspond to units of measure, techniques, properties or compounds as follows: "RT" or "Rt" means retention time, "min" means minutes, "h" means hour(s), "µL" means microliter(s), "mL" means milliliter(s), "mM" means millimolar, "M" means molar, "mmole" means millimole(s), "eq" means molar equivalent(s). "High Pressure Liquid Chromatography" or "High Performance Liquid Chromatography" are abbreviated HPLC.

The term "alkyl" refers to linear, branched or cyclic, saturated hydrocarbon groups. Examples of alkyl groups include, without limitation, methyl, ethyl, n-propyl, isopropyl, n-butyl, pentyl, hexyl, heptyl, cyclopentyl, cyclohexyl, cyclohexylmethyl, and the like. Alkyl groups may optionally be substituted with substituents selected from acyl, amino, acylamino, acyloxy, carboalkoxy, carboxy, carboxyamido, cyano, halo, hydroxyl, nitro, thiol, alkyl, alkenyl, alkynyl, cycloalkyl, heterocycloalkyl, aryl, heteroaryl, alkoxy, aryloxy, sulfinyl, sulfonyl, oxo, guanidino and formyl.

The term "$C_{1-n}$alkyl", wherein n is an integer from 2 to 12, refers to an alkyl group having from 1 to the indicated "n" number of carbons. The $C_{1-n}$alkyl can be cyclic or a straight or branched chain.

The term "linear $C_{1-n}$alkyl", wherein n is an integer from 2 to 10, refers to an alkyl group having from 1 to the indicated "n" number of carbons and being linear, i.e. not cyclic or branched in the vicinity of the attached atom (herein the nitrogen). The $C_{1-n}$alkyl can optionally be substituted with small groups such as acyl, amino, acylamino, acyloxy, carboalkoxy, carboxy, carboxyamido, cyano, halo, hydroxyl, nitro, thiol alkoxy, sulfinyl, sulfonyl, oxo, guanidino and formyl.

The term "alkenyl" refers to linear, branched or cyclic unsaturated hydrocarbon groups containing, from one to six carbon-carbon double bonds. Examples of alkenyl groups include, without limitation, vinyl, 1-propene-2-yl, 1-butene-4-yl, 2-butene-4-yl, 1-pentene-5-yl and the like. Alkenyl groups may optionally be substituted with substituents selected from acyl, amino, acylamino, acyloxy, carboalkoxy, carboxy, carboxyamido, cyano, halo, hydroxyl, nitro, thiol, alkyl, alkenyl, alkynyl, cycloalkyl, heterocycloalkyl, aryl, heteroaryl, alkoxy, aryloxy, sulfinyl, sulfonyl, formyl, oxo and guanidino. The double bond portion(s) of the unsaturated hydrocarbon chain may be either in the cis or trans configuration.

The term "$C_{2-n}$alkenyl", wherein n is an integer from 3 to 12, refers to an alkenyl group having from 2 to the indicated "n" number of carbons. The $C_{2-n}$alkenyl can be cyclic or a straight or branched chain.

The term "alkynyl" refers to linear, branched or cyclic unsaturated hydrocarbon groups containing at least one carbon-carbon triple bond. Examples of alkynyl groups include, without limitation, ethynyl, 1-propyne-3-yl, 1-butyne-4-yl, 2-butyne-4-yl, 1-pentyne-5-yl and the like. Alkynyl groups may optionally be substituted with substituents selected from acyl, amino, acylamino, acyloxy, carboalkoxy, carboxy, carboxyamido, cyano, halo, hydroxyl, nitro, thiol, alkyl, alkenyl, alkynyl, cycloalkyl, heterocycloalkyl, aryl, heteroaryl, alkoxy, aryloxy, sulfinyl, sulfonyl, formyl, oxo and guanidine.

The term "$C_{2-n}$alkynyl", wherein n is an integer from 3 to 12, refers to an alkynyl group having from 2 to the indicated "n" number of carbons. The $C_{2-n}$alkynyl can be cyclic or a straight or branched chain.

The term "cycloalkyl" or "cycloalkyl ring" refers to an alkyl group, as defined above, further comprising a saturated or partially unsaturated carbocyclic ring in a single or fused carbocyclic ring system having from three to fifteen ring members. Examples of cycloalkyl groups include, without limitation, cyclopropyl, cyclobutyl, cyclopentyl, cyclopenten-1-yl, cyclopenten-2-yl, cyclopenten-3-yl, cyclohexyl, cyclohexen-1-yl, cyclohexen-2-yl, cyclohexen-3-yl, cycloheptyl, bicyclo[4,3,0]nonanyl, norbornyl, and the like. Cycloalkyl groups may optionally be substituted with substituents selected from acyl, amino, acylamino, acyloxy, carboalkoxy, carboxy, carboxyamido, cyano, halo, hydroxyl, nitro, thiol, alkyl, alkenyl, alkynyl, cycloalkyl, heterocycloalkyl, aryl, heteroaryl, alkoxy, aryloxy, sulfinyl, sulfonyl and formyl.

The term "$C_{3-n}$cycloalkyl", wherein n is an integer from 4 to 15, refers to a cycloalkyl ring or ring system or having from 3 to the indicated "n" number of carbons.

The term "heterocycloalkyl", "heterocyclic" or "heterocycloalkyl ring" refers to a cycloalkyl group, as defined above, further comprising one to four hetero atoms (e.g. N, O, S, P) or hetero groups (e.g. NH, $NR^X$, $PG_2$, $SO_2$) in a single or fused heterocyclic ring system having from three to fifteen ring members (e.g. tetrahydrofuranyl has five ring members, including one oxygen atom). Examples of a heterocycloalkyl, heterocyclic or heterocycloalkyl ring include, without limitation, pyrrolidino, tetrahyd rofu ranyl, tetrahyd rod ith enyl, tetrahyd ropyranyl, tetrahyd roth opyranyl, piperidino, morpholino, thiomorpholino, thioxanyl, piperazinyl, azetidinyl, oxetanyl, thietanyl, homopiperidinyl, oxepanyl, thiepanyl, oxazepinyl, diazepinyl, thiazepinyl, 1 ,2,3,6-tetrahydropyridinyl, 2-pyrrolinyl, 3-pyrrolinyl, indolinyl, 2H-pyranyl, 4H-pyranyl, dioxanyl, 1 ,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3,1,0]hexanyl, 3-azabicyclo[4,1,0]heptanyl, 3H-indolyl, quinolizinyl, and glucuronide. The foregoing heterocycloalkyl groups, as derived from the compounds listed above, may be C-attached or N-attached where such is possible. Heterocycloalkyl, heterocyclic or heterocycloalkyl ring may optionally be substituted with substituents selected from acyl, amino, acylamino, acyloxy, oxo, thiocarbonyl, imino, carboalkoxy, carboxy, carboxyamido, cyano, halo, hydroxyl, nitro, thiol, alkyl, alkenyl, alkynyl, cycloalkyl, heterocycloalkyl, aryl, heteroaryl, alkoxy, aryloxy, sulfinyl, sulfonyl and formyl.

The term "$C_{3-n}$heterocycloalkyl", wherein n is an integer from 4 to 15, refers to an heterocycloalkyl group having from 3 to the indicated "n" number of atoms in the cycle and -at least one hetero group as defined above.

The terms "halo" or "halogen" refers to bromine, chlorine, fluorine or iodine substituents.

The term "aryl" or "aryl ring" refers to common aromatic groups having "4n+2" Π(pi) electrons, wherein n is an integer from 1 to 3, in a conjugated monocyclic or polycyclic system and having from five to fourteen ring atoms. Aryl may be directly attached, or connected via a $C_{1-3}$alkyl group (also referred to as aralkyl). Examples of aryl include, without limitation, phenyl, benzyl, phenethyl, 1-phenylethyl, tolyl, naphthyl, biphenyl, terphenyl, and the like. Aryl groups may optionally be substituted with one or more substituent group selected from acyl, amino, acylamino, acyloxy, azido, alkythio, carboalkoxy, carboxy, carboxyamido, cyano, halo, hydroxyl, nitro, thiol, alkyl, alkenyl, alkynyl, cycloalkyl, heterocyclyl, aryl, heteroaryl, alkoxy, aryloxy, sulfinyl, sulfonyl and formyl.

The term "$C_{5-n}$aryl", wherein n is an integer from 6 to 14, refers to an aryl group having from 6 to the indicated "n" number of atoms, including carbon, nitrogen, oxygen and sulfur. The $C_{5-n}$aryl can be mono or polycyclic.

The term "heteroaryl" or "heteroaryl ring" refers to an aryl ring, as defined above, further containing one to four heteroatoms selected from oxygen, nitrogen, sulphur or phosphorus. Examples of heteroaryl include, without limitation, pyridyl, imidazolyl, pyrimidinyl, pyrazolyl, triazolyl, tetrazolyl, furyl, thienyl, isooxazolyl, thiazolyl, oxazolyl, isothiazolyl, pyrrollyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazol inyl, quinoxalinyl, naphthyridinyl, and furopyridinyl groups. Heteroaryl may optionally be substituted with one or more substituent group selected from acyl, amino, acylamino, acyloxy, azido, alkythio, carboalkoxy, carboxy, carboxyamido, cyano, halo, hydroxyl, nitro, thiol, alkyl, alkenyl, alkynyl, cycloalkyl, heterocyclyl, aryl, heteroaryl, alkoxy, aryloxy, sulfinyl, sulfonyl and formyl. Heteroaryl may be directly attached, or connected via a $C_{1-3}$alkyl group (also referred to as heteroaralkyl). The foregoing heteroaryl groups, as derived from the compounds listed above, may be C-attached or N-attached where such is possible.

The term "$C_{5-n}$heteroaryl", wherein n is an integer from 6 to 14, refers to an heteroaryl group having from 5 the indicated "n" number of atoms, including carbon, nitrogen, oxygen and sulphur atoms. The $C_{5-n}$heteroaryl can be mono or polycyclic.

The compounds of the present invention can possess one or more asymmetric carbon atoms and can exist as optical isomers forming mixtures of racemic or non-racemic compounds. The compounds of the present invention are useful as single isomers or as a mixture of stereochemical isomeric forms. Diastereoisomers, i.e., nonsuperimposable stereochemical isomers, can be separated by conventional means such as chromatography, distillation, crystallization or sublimation. The optical isomers can be obtained by resolution of the racemic mixtures according to conventional processes, including chiral chromatography (e.g. HPLC), immunoassay techniques, or the use of covalently (e.g. Mosher's esters) or non-covalently (e.g. chiral salts) bound chiral reagents to respectively form a diastereomeric ester or salt, which can be further separated by conventional methods, such as chromatography, distillation, crystallization or sublimation. The chiral ester or salt is then cleaved or exchanged by conventional means, to recover the desired isomer(s).

The invention encompasses isolated or purified compounds. An "isolated" or "purified" compound refers to a compound substantially free of other molecules. An "isolated" or "purified" compound is substantially free of other molecules when it is at least about 80%, at least about 90%, at least about 91%, at least about 92%, at least about 93%, at least about 94%, at least about 95%, at least about 96%, at least about 97%, at least about 98%, at least about 99% of 100% pure, measured by weight.

The term "pharmaceutically acceptable salt" refers to nontoxic salts synthesized from a compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, methanol, ethanol, isopropanol, or acetonitrile are preferred. Another method for the preparation of salts is by the use of ion exchange resins. The term "pharmaceutically acceptable salt" includes both acid addition salts and base addition salts of phosphate prodrugs or solvates thereof. The nature of the salt is not critical, provided that it is pharmaceutically acceptable. Exemplary acids used in acid addition salts include, without limitation, hydrochloric, hydrobromic, hydroiodic, nitric, carbonic, sulfuric, sulfonic, phosphoric, formic, acetic, citric, tartaric, succinic, oxalic, malic, glutamic, propionic, glycolic, gluconic, maleic, embonic (pamoic), methanesulfonic, ethanesulfonic, 2-hydroxyethanesulfonic, pantothenic, benzenesulfonic, toluenesulfonic, sulfanilic, mesylic, cyclohexylaminosulfonic, stearic, algenic, β-hydroxybutyric, malonic, galactaric, galacturonic acid and the like. Suitable pharmaceutically acceptable base addition salts include, without limitation, metallic salts made from alkali metals (e.g. lithium, sodium and potassium), alkaline earth metals (e.g. calcium and magnesium), and other physiologically compatible metals such as aluminum and zinc or organic salts, such as those made from ammonia, tetramethylammonium, diethylamine, trimethylamine, triethylamine, morpholine, pyridine, piperidine, piperazine, picoline, dicyclohexylamine, 2-hydroxyethylamine, bis(2-hydroxyethyl)amine, tris(2-hydroxyethyl) amine, tris(hydroxymethyl)aminomethane, dibenzylpiperidine, N-benzyl-β-phenethylamine, N,N'-dibenzylethylenediamine, N,N'-benzylphenethylamine, chloroprocaine, procaine, choline, ethylenediamine, glucamine, N-methylglucamine (meglumine), collidine, quinoline, ornithine, arginine, lysine, and the like. Examples of pharmaceutically acceptable salts are also listed in Berge et al (1977), *Journal of Pharmaceutical Sciences*, vol 66, no 1, pp 1-19, and in the *Handbook of Pharmaceutical Salts*, P. Heinrich Stahl and Camille G. Wermuth (Eds), 2002, VHCA (Switzerland) and Wiley-VCH (Gemany), the content of which are incorporated herein by reference in their entirety.

The term "pharmaceutically acceptable solvate" refers to a physical association of a compound of this invention with one or more solvent molecules, whether organic or inorganic. This physical association includes hydrogen bonding. In certain instances the solvate will be capable of isolation, for example when one or more solvent molecules are incorporated in the crystal lattice of the crystalline solid. "Solvate" encompasses both solution-phase and isolable solvates. Exemplary solvates include hydrates, ethanolates, methanolates, hemiethanolates, and the like.

II. Compounds of the Invention

In one aspect, the invention relates to novel farnesyl dibenzodiazepinone prodrugs, and to pharmaceutically acceptable salts and solvates thereof, referred to herein as the compounds of the invention.

The compounds of the invention may be characterized as phosphate prodrugs obtained by phosphorylation of Compound 1.

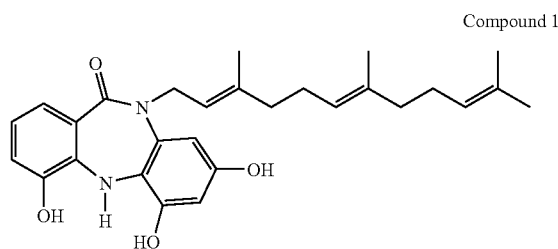

Compound 1

The phosphate prodrugs of the invention may be characterized by any one of their physicochemical and spectral properties, such as mass and NMR, detailed in Example 2 through Example 4 below.

In another aspect, the invention relates to farnesyl dibenzodiazepinone prodrugs, represented by Formula I:

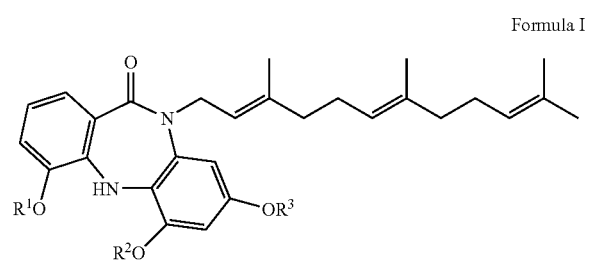

Formula I wherein, $R^1$ $R^2$ and $R^3$ are each independently selected from the group consisting of H and a phosphate of formula II:

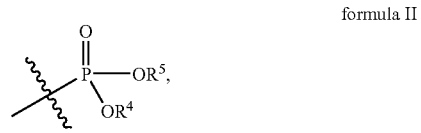

formula II wherein at least one of $R^1$, $R^2$, or $R^3$ is a phosphate of formula II;

$R^4$ and $R^5$ are each independently selected from the group consisting of H, $C_{1-10}$alkyl, $C_{2-10}$alkenyl, $C_{2-10}$alkynyl, $C_{6-10}$aryl, $C_{5-10}$heteroaryl, $C_{3-10}$cycloalkyl, and $C_{3-10}$heterocycloalkyl;

wherein, when either or both of $R^4$ and $R^5$ comprises an alkyl, alkenyl, alkynyl, aryl, heteroaryl, cycloalkyl, or heterocycloalkyl group, then the alkyl, alkenyl, alkynyl, aryl, heteroaryl, cycloalkyl, or heterocycloalkyl group is optionally substituted with one or more substituents selected from the group consisting of acyl, amino, acylamino, acyloxy, carboalkoxy, carboxy, carboxyamido, cyano, halo, hydroxyl, nitro, thiol $C_{1-6}$alkyl, $C_{2-7}$alkenyl, C27alkynyl, $C_{3-10}$cycloalkyl, $C_{3-10}$heterocycloalkyl, $C_{6-10}$aryl, $C_{5-10}$heteroaryl, alkoxy, aryloxy, sulfinyl, sulfonyl, oxo, guanidino and formyl;

or a pharmaceutically acceptable salt or solvate thereof.

In further aspect, the invention relates to farnesyl dibenzodiazepinone prodrugs represented by Formula I:

Formula I

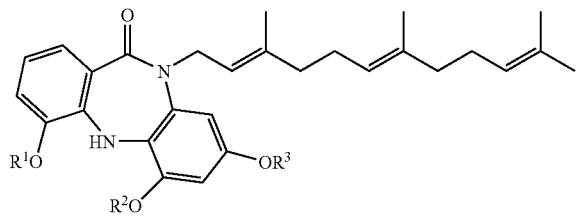

wherein,
$R^1$ $R^2$ and $R^3$ are each independently selected from the group consisting of H and a phosphate of formula II:

formula II

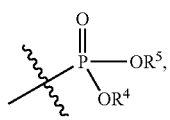

wherein at least one of $R^1$, $R^2$, or $R^3$ is a phosphate of formula II;

$R^4$ and $R^5$ are each independently selected from the group consisting of H, $C_{1-10}$alkyl, $C_{2-10}$alkenyl, $C_{2-10}$alkynyl, $C_{6-10}$aryl, $C_{5-10}$heteroaryl, $C_{3-10}$cycloalkyl, and $C_{3-10}$heterocycloalkyl;

wherein, at least one of $R^4$ or $R^5$ is H in at least one phosphate of formula II;

wherein, when either or both of $R^4$ and $R^5$ comprises an alkyl, alkenyl, alkynyl, aryl, heteroaryl, cycloalkyl, or heterocycloalkyl group, then the alkyl, alkenyl, alkynyl, aryl, heteroaryl, cycloalkyl, or heterocycloalkyl group is optionally substituted with one or more substituents selected from the group consisting of acyl, amino, acylamino, acyloxy, carboalkoxy, carboxy, carboxyamido, cyano, halo, hydroxyl, nitro, thiol, $C_{1-6}$alkyl, $C_{2-7}$alkenyl, C27alkynyl, $C_{3-10}$cycloalkyl, $C_{3-10}$heterocycloalkyl, $C_{6-10}$aryl, $C_{5-10}$heteroaryl, alkoxy, aryloxy, sulfinyl, sulfonyl, oxo, guanidino and formyl;

or a pharmaceutically acceptable salt or solvate thereof.

In one embodiment of Formula I, $R^1$ is H, and all other groups are as previously disclosed. In another embodiment, $R^2$ is H, and all other groups are as previously disclosed. In another embodiment, $R^3$ is H, and all other groups are as previously disclosed. In another embodiment, $R^1$ and $R^2$ are each H, and all other groups are as previously disclosed. In another embodiment, $R^1$ and $R^3$ are each H, and all other groups are as previously disclosed. In another embodiment, $R^2$ and $R^3$ are each H, and all other groups are as previously disclosed. In another embodiment, $R^1$, $R^2$ and $R^3$ are each a phosphate of formula II, and all other groups are as previously disclosed. The invention encompasses all pharmaceutically acceptable salts and solvates of the foregoing compounds.

In another embodiment, the compound of the invention is a pharmaceutically acceptable salt of a compound of Formula I, and is made from an alkali metals (e.g. lithium, sodium and potassium), alkaline earth metals (e.g. calcium and magnesium), and other physiologically compatible metals such as aluminum and zinc or organic salts, such as those made from ammonia, tetramethylammonium, diethylamine, trimethylamine, triethylamine, morpholine, pyridine, piperidine, piperazine, picoline, dicyclohexylamine, 2-hydroxyethylamine, bis(2-hydroxyethyl)amine, tris(2-hydroxyethyl)amine, tris(hydroxymethyl)aminomethane, dibenzylpiperidine, N-benzyl-β-phenethylamine, N,N'-dibenzylethylenediamine, N,N'-benzylphenethylamine, chloroprocaine, procaine, choline, ethylenediamine, glucamine, N-methylglucamine (meglumine), collidine, quinoline, ornithine, arginine, lysine, and the like. In yet another embodiment, the salt is a mono-salt, a di-salt, a tri-salt, a tetra-salt, or a hexa-salt.

The following are exemplary compounds of the invention, such named compounds are not intended to limit the scope of the invention in any way:

Compound 2

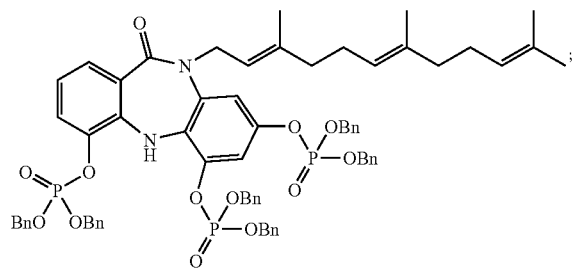

Compound 3

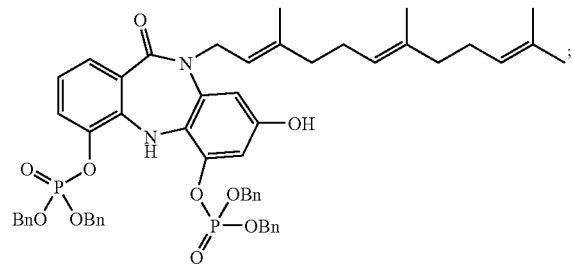

Compound 4

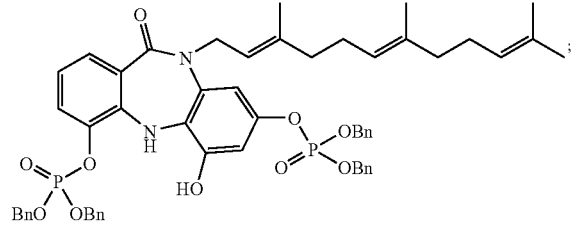

Compound 5

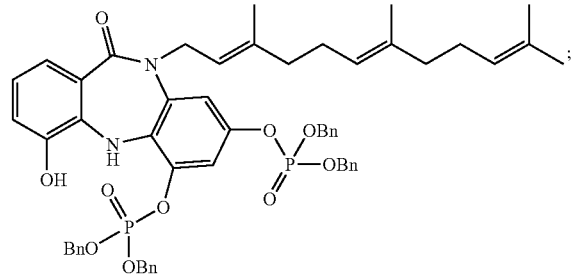

-continued
Compound 6
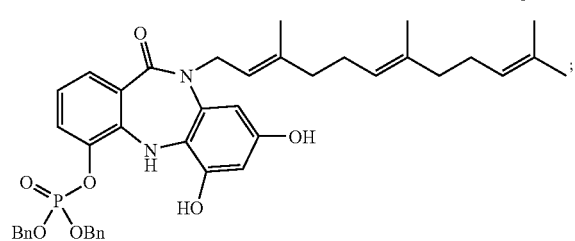
Compound 7
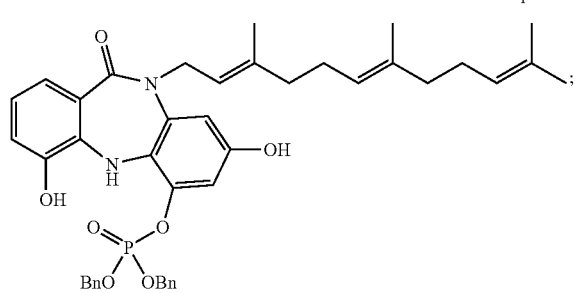
Compound 8
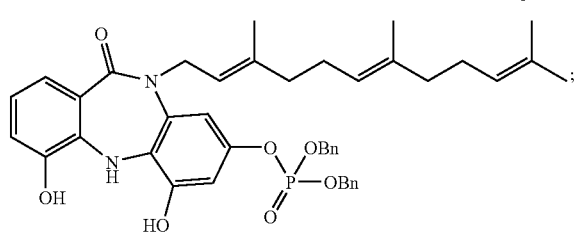
Compound 9
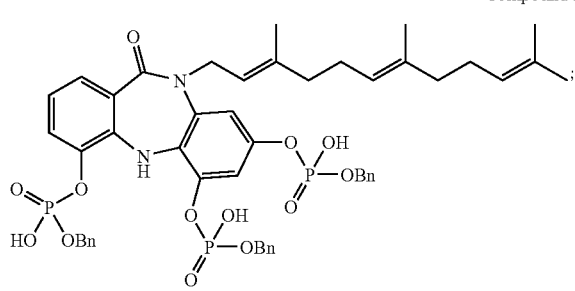
Compound 10
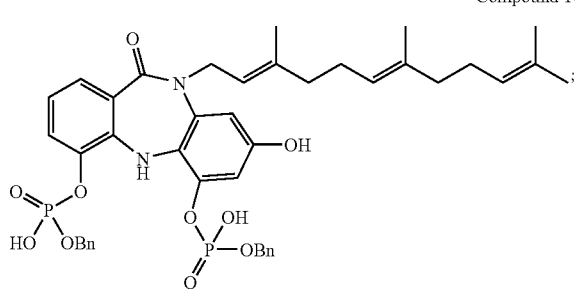
-continued
Compound 11
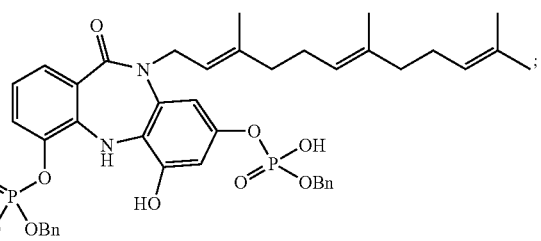
Compound 12
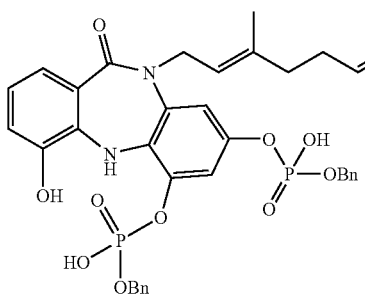
Compound 13
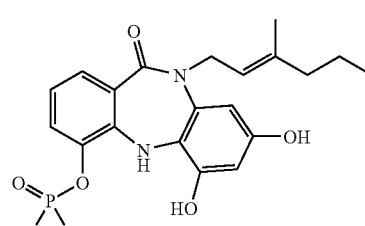
Compound 14
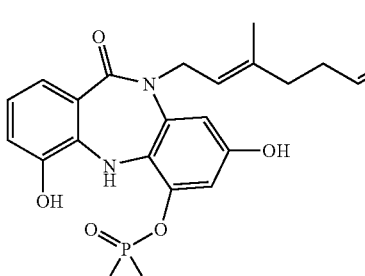
Compound 15
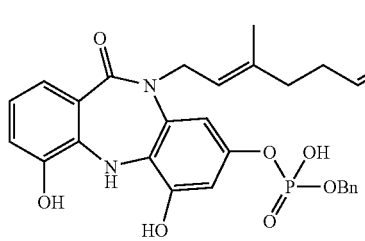

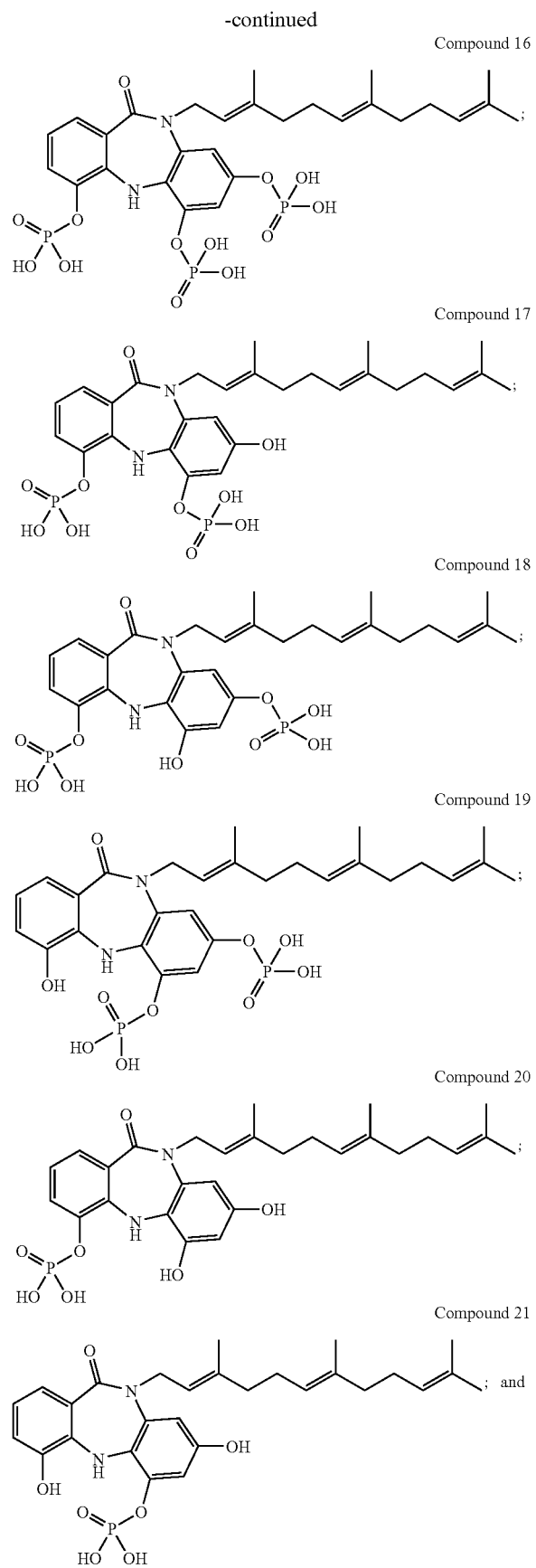

Compound 16

Compound 17

Compound 18

Compound 19

Compound 20

Compound 21

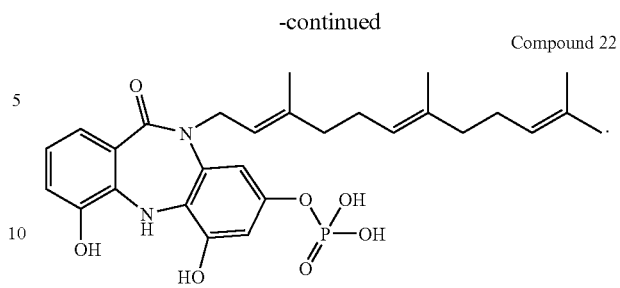

Compound 22

Pharmaceutically acceptable salt or solvate any one of Compounds 2 to 22 are also encompassed within the scope of the invention. In another embodiment, the compound is selected from Compound 9 to 22 or a pharmaceutically acceptable salt or solvate thereof. In another embodiment, the compound is selected from Compounds 16-22 or a pharmaceutically acceptable salts or solvate thereof. In another embodiment, the compound is selected from Compound 9 and 16-21 or a pharmaceutically acceptable salt or solvate thereof. Preferred salts of the compounds of the present invention include sodium salts, potassium salts, ammonia salts and methyl N-pyridium salts. Certain embodiments may exclude one or more of the compounds of Formula I.

Each of the compounds of this invention may be formulated into pharmaceutical compositions, in combination with a pharmaceutically acceptable carrier, as discussed in Section IV below.

III. Methods of Producing Dibenzodiazepinone Phosphate Prodrugs

The farnesyl dibenzodiazepinone Compound 1 is biosynthesized by microorganisms and isolated as described in, for example, US Patent Application publication no 2005/0043297. Compound 1 is subjected to random and/or directed chemical modifications to form phosphate prodrugs. The farnesyl dibenzodiazepinone may be modified by one or more chemical modification steps, using methods known in the art and described herein. Examples of chemical modifications procedures are also provided in Examples 2 to 4.

Dibenzodiazepinone phosphate prodrugs of Compound 1, for example those identified herein as the compounds of Formula I and their derivatives, including Compounds 2 to 22, are generated by standard organic chemistry approaches. General principles of organic chemistry required for making and manipulating the compounds described herein, including functional moieties, reactivity and common protocols are described, for example, in "Advanced Organic Chemistry," 4th Edition by Jerry Mar. (1992), Wiley-Interscience, USA, incorporated herein by reference in its entirety. Phosphorylation procedures are also described, for example, in Silverberg et al (1996), *Tet. Lett.*, vol. 37,771-774; in Hwang and Cole (2004), *Org. Lett.*, vol 6, no 10, 1555-1556; and in U.S. Pat. No. 5,561,122 (issued to Pettit et al).

In addition, it will be appreciated by one of ordinary skill in the art that the synthetic methods described herein may use a variety of protecting groups, whether or not they are explicitly described. A "protecting group" as used herein means a moiety used to block one or more functional moieties such as reactive groups including oxygen, sulfur or nitrogen, so that a reaction can be carried out selectively at another reactive site in a polyfunctional compound. General principles for the use of protective groups, their applicability to specific functional groups and their uses are described for example in T. H. Greene and P. G. M. Wuts, Protective Groups in Organic Synthesis, 3rd Edition, John Wiley & Sons, New York (1999), incorporated herein by reference in its entirety.

Oxygen atoms (from alcohols, phenols or phosphates) are protected with, for example: silyl ethers (e.g TMS: trimethylsilyl, TIPS: triisopropylsilyl), acetals (e.g. MOM: methyloxymethyl, BOM: benzyloxymethyl), and other groups (e.g. acetate (Ac), benzoyl (Bz), and benzyl (Bn)). Groups such as Ac and Bz are more appropriate for alcohols and phenols than phosphates. Oxygen atoms are deprotected by conditions such as: TBAF (tetrabutylammonium fluoride) for silyl ethers, aqueous acid catalysis for acetals and esters, saponification for esters (Ac and Bz), and hydrogenolysis for Bn and BOM. Nitrogen atom (from amine) is protected using standard amino acid protecting groups, for example, carbamates (e.g. t-butyl (BOC) and benzyl (CBZ)), fluorene derivatives (e.g. FMOC: N-(9-fluorenylmethoxycarbonyl)-), etc. Nitrogen atom is deprotected by conditions such as: acid hydrolysis for BOC, hydrogenolysis for CBZ, or base treatment for FMOC. Protection and deprotection conditions are demonstrated in the Greene et al reference above.

Those skilled in the art will readily appreciate that many synthetic chemical processes may be used to produce prodrugs of Compound 1. The following scheme is exemplary of the routine chemical modifications that may be used to produce compounds of Formula I. Any chemical synthetic process known to a person skilled in the art providing the structures described herein may be used and are therefore comprised in the present invention.

Scheme 1: O-Phosphorylation

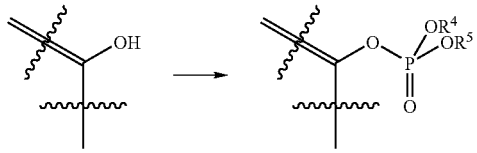

wherein, $R^4$ and $R^5$ are as previously defined.

In Scheme 1, phenols in positions 4, 6 and 8 (for position numbers, see Example 2) are independently phosphorylated to produce a phosphate ester and are optionally partially or fully deprotected to produce a free acid or a base addition phosphate salt either in situ or in a separate step. The phosphorylation step is accomplished by reacting Compound 1, or a partially protected analog, with a phosphorylating agent $XP(O)OR^4OR^5$ (such as bis(2,2,2-trichloroethyl)phosphorochloridate) or a phosphite $P(OH)OR^4OR^5$ (such as dibenzylphosphite). The protecting groups on the phosphate ester and other protecting groups are optionally cleaved to produce partially deprotected (one of $R^4$ or $R^5$ is H) or fully deprotected (both $R^4$ and $R^5$ are H) using the appropriate conditions depending on the nature of the protecting group. Such conditions include, for example, reacting the phosphate ester with zinc dust with glacial acetic acid in pyridine to remove trichloroethyl groups, or using controlled catalytic hydrogenation to cleave a benzyl group. Monodeprotection of a dibenzylphosphate group was also performed using sodium iodide in acetonitrile. The product obtained from the deprotection may be the free acid or may be a base addition salt formed in situ. The salt may also be formed in a separate step from the free acid by reacting with the corresponding base, or by exchanging a salt for another using known techniques.

Scheme 1 is used to obtain, for example, Compounds 2 to 8 from Compound 1, Compounds 9 and 16 from Compound 2, Compounds 10 and 17 from Compound 3, Compounds 11 and 18 from Compound 4, Compounds 12 and 19 from Compound 5, Compounds 13 and 20 from Compound 6, Compounds 14 and 21 from Compound 7, and Compounds 15 and 22 from Compound 8, and to produce any of the compounds of Formula I.

IV. Pharmaceutical Compositions Comprising the Compounds of the Invention

The invention provides a pharmaceutical composition comprising a compound of Formula I, or a pharmaceutically acceptable salt or solvate thereof, in combination with a pharmaceutically acceptable carrier. The pharmaceutical composition comprising a phosphate prodrug is useful for treating diseases and disorders associated with uncontrolled cellular growth and proliferation, such as a neoplastic condition. The pharmaceutical composition is also useful in treating other diseases and disorders, including inflammation, autoimmune diseases, infections, neurodegenerative diseases and stress. The pharmaceutical composition comprising a phosphate prodrug may be packaged into a convenient commercial package providing the necessary materials, such as the pharmaceutical composition and written instructions for its use in treating a neoplastic condition, in a suitable container.

The compounds of the present invention, or pharmaceutically acceptable salts or solvates thereof, can be formulated for oral, sublingual, intranasal, intraocular, rectal, transdermal, mucosal, topical or parenteral administration for the therapeutic or prophylactic treatment of neoplastic and proliferative diseases and disorders. Parenteral modes of administration include without limitation, intradermal, subcutaneous (s.c., s.q., sub-Q, Hypo), intramuscular (i.m.), intravenous (i.v.), intraperitoneal (i.p.), intra-arterial, intramedulary, intracardiac, intra-articular (joint), intrasynovial (joint fluid area), intracranial, intraspinal, and intrathecal (spinal fluids). Any known device useful for parenteral injection or infusion of drug formulations can be used to effect such administration. Compounds of the present invention can be mixed with conventional pharmaceutical carriers and excipients to form the pharmaceutical compositions of the present invention, and such compositions can be used in the form of solutions, emulsions, tablets, capsules, soft gels, elixirs, suspensions, syrups, wafers and the like. The pharmaceutical compositions comprising a compound of the present invention will contain from about 0.1% to about 99.9%, about 1% to about 98%, about 5% to about 95%, about 10% to about 80% or about 15% to about 60% by weight of the compound. In particular embodiments, the pharmaceutical compositions comprising a compound of the present invention will contain greater than about 50%, 60%, 70%, 80%, 90%, 91%, 92%, 93%, 94%, 95%, 96%, 97%, 98%, or 99% by weight of the compound.

The pharmaceutical compositions disclosed herein are prepared in accordance with standard procedures and are administered at dosages that are selected to reduce, prevent, or eliminate cancer. (See, e.g., *Remington's Pharmaceutical Sciences*, Mack Publishing Company, Easton, Pa.; and Goodman and Gilman, *Pharmaceutical Basis of Therapeutics*, Pergamon Press, New York, N.Y., the contents of which are incorporated herein by reference, for a general description of the methods for administering various agents for human therapy).

As used herein, the term "unit dosage" refers to physically discrete units suitable as unitary dosages for human subjects and other mammals, each unit containing a predetermined quantity of phosphate prodrug calculated to produce the desired therapeutic effect, in association with a suitable pharmaceutically acceptable carriers. In one embodiment, the unit dosage contains an amount of prodrug equivalent to an amount of active metabolite of about 10 mg to about 3000 mg. In another embodiment, the unit dosage contains an amount of prodrug equivalent to an amount of active metabolite of about 20 to about 2000 mg, preferably about 50 to about 1000 mg, more preferably about 100 to about 500 mg. In another embodiment, the unit dosage contains an amount of about 100 mg to about 4000 mg of the prodrug. In another embodiment, the unit dosage contains an amount of about 20 to about 4000 mg of the prodrug, preferably about 50 to about 2000 mg, more preferably about 100 to about 1000 mg. The compositions of the present invention can be delivered using controlled or sustained release delivery systems (e.g., bioerodable matrices). Exemplary delayed release delivery systems for drug delivery that are suitable for administration of the compositions of the invention are described in U.S. Pat. No. 4,452,775 (issued to Kent), U.S. Pat. No. 5,039,660 (issued to Leonard), and U.S. Pat. No. 3,854,480 (issued to Zaffaroni), incorporated herein by reference in their entirety.

The pharmaceutically acceptable compositions of the present invention comprise one or more compounds of the present invention in association with one or more non-toxic, pharmaceutically acceptable carriers and/or diluents and/or adjuvants and/or excipients, collectively referred to herein as "carrier" materials, and if desired other active ingredients. Pharmaceutically acceptable carriers include, for example, solvents, vehicles or medium such as saline, buffered saline, dextrose, water, glycerol, ethanol, propylene glycol, polysorbate 80 (Tween-80™), poly(ethylene) glycol 300 and 400 (PEG 300 and 400), PEGylated castor oil (E.g. Cremophor EL), poloxamer 407 and 188, hydrophobic carriers, and combinations thereof. Hydrophobic carriers include, for example, fat emulsions, lipids, PEGylated pholpholids, polymer matrices, biocompatible polymers, liposheres, vesicles, particles, and liposomes. The term specifically excludes cell culture medium.

Excipients or adjuvants included in a formulation have different purposes depending, for example on the nature of the drug, and the mode of administration. Examples of generally used excipients include, without limitation: stabilizing agents, solubilizing agents and surfactants, buffers, antioxidants and preservatives, tonicity agents, bulking agents, lubricating agents, emulsifiers, suspending or viscosity agents, inert diluents, fillers, disintegrating agents, binding agents, wetting agents, lubricating agents, antibacterials, chelating agents, sweetners, perfuming agents, flavouring agents, coloring agents, administration aids, and combinations thereof.

The compositions may contain common carriers and excipients, such as cornstarch or gelatin, lactose, sucrose, microcrystalline cellulose, kaolin, mannitol, dicalcium phosphate, sodium chloride, alginic acid, croscarmellose sodium, and sodium starch glycolate.

Formulations for parenteral administration can be in the form of aqueous or non-aqueous isotonic sterile injection solutions, suspensions or fat emulsions, comprising a prodrug of this invention, or a pharmaceutically acceptable salt or solvate thereof. The parenteral form used for injection must be fluid to the extent that easy syringability exists. These solutions or suspensions can be prepared from sterile concentrated liquids, powders or granules. The prodrugs can be dissolved in a carrier such as a solvent or vehicle, for example, water, saline, dextrose, polyethylene glycol, propylene glycol, ethanol, corn oil, benzyl alcohol, glycofurol, N,N-dimethylacetamide, N-methylpyrrolidone, glycerine, glycerol, hydrophobic carriers, and combinations thereof.

Excipients used in parenteral preparations also include, without limitation, stabilizing agents (e.g. carbohydrates, amino acids and polysorbates), solubilizing agents (e.g. cetrimide, sodium docusate, glyceryl monooleate, polyvinylpyrolidone (PVP) and polyethylene glycol (PEG)), surfactants (e.g. polysorbates, tocopherol PEG succinate, poloxamer and Cremophor™), buffers (e.g. acetates, citrates, phosphates, tartrates, lactates, succinates, amino acids and the like), antioxidants and preservatives (e.g. BHA, BHT, gentisic acids, vitamin E, ascorbic acid, sodium ascorbate and sulfur containing agents such as sulfites, bisulfites, metabisulfites, thioglycerols, thioglycolates and the like), tonicity agents (for adjusting physiological compatibility), suspending or viscosity agents, antibacterials (e.g. thimersol, benzethonium chloride, benzalkonium chloride, phenol, cresol and chlorobutanol), chelating agents, and administration aids (e.g. local anesthetics, anti-inflammatory agents, anti-clotting agents, vaso-constrictors for prolongation and agents that increase tissue permeability), and combinations thereof.

Parenteral formulations using hydrophobic carriers include, for example, fat emulsions and formulations containing lipids, lipospheres, vesicles, particles and liposomes. Fat emulsions include in addition to the above-mentioned excipients, a lipid and an aqueous phase, and additives such as emulsifiers (e.g. phospholipids, poloxamers, polysorbates, and polyoxyethylene castor oil), and osmotic agents (e.g. sodium chloride, glycerol, sorbitol, xylitol and glucose). Liposomes include natural or derived phospholipids and optionally stabilizing agents such as cholesterol.

In another embodiment, the parenteral unit dosage form of the prodrug can be a ready-to-use solution of the prodrug in a suitable carrier in sterile, hermetically sealed ampoules or in sterile pre-loaded syringes. The suitable carrier optionally comprises any of the above-mentioned excipients.

Alternatively, the unit dosage of the prodrug of the present invention can be in a concentrated liquid, powder or granular form for ex tempore reconstitution in the appropriate pharmaceutically acceptable carrier at the time of delivery. In addition to the above-mentioned excipients, powder forms optionally include bulking agents (e.g. mannitol, glycine, lactose, sucrose, trehalose, dextran, hydroxyethyl starch, ficoll and gelatin), and cryo or lyoprotectants.

For example, in intravenous (IV) use, a sterile formulation of the prodrug of Formula I, or a pharmaceutically acceptable salt or solvate thereof, and optionally one or more additives, including solubilizers or surfactants, can be dissolved or suspended in any of the commonly used intravenous fluids and administered by infusion. Intravenous fluids include, without limitation, physiological saline, phosphate buffered saline, 5% dextrose or Ringer's™ solution.

In another example, in intramuscular preparations, a sterile formulation of the prodrug of the present invention or suitable soluble salts or solvates forming the prodrug, can be dissolved and administered in a pharmaceutical diluent such as Water-for-Injection (WFI), physiological saline or 5% dextrose. A suitable insoluble form of the prodrug may be prepared and administered as a suspension in an aqueous base or a pharmaceutically acceptable oil base, e.g. an ester of a long chain fatty acid such as ethyl oleate.

For oral use, solid formulations such as tablets and capsules are particularly useful. Sustained released or enterically coated preparations may also be devised. For pediatric and geriatric applications, suspension, syrups and chewable tablets are especially suitable. For oral administration, the pharmaceutical compositions are in the form of, for example, tablets, capsules, suspensions or liquid syrups or elixirs, wafers and the like. For general oral administration, excipient or additives include, but are not limited to inert diluents, fillers, disintegrating agents, binding agents, wetting agents, lubricating agents, sweetening agents, flavoring agents, coloring agents and preservatives.

The oral pharmaceutical composition is preferably made in the form of a unit dosage containing a therapeutically-effective amount of the phosphate prodrug. Examples of such dosage units are tablets and capsules. For therapeutic purposes, the tablets and capsules which can contain, in addition to the prodrug, conventional carriers such as: inert diluents (e.g., sodium and calcium carbonate, sodium and calcium phosphate, and lactose), binding agents (e.g., acacia gum, starch, gelatin, sucrose, polyvinylpyrrolidone (Povidone), sorbitol, tragacanth methylcellulose, sodium carboxymethylcellulose, hydroxypropyl methylcellulose, and ethylcellulose), fillers (e.g., calcium phosphate, glycine, lactose, maize-starch, sorbitol, or sucrose), wetting agents, lubricating agents (e.g., metallic stearates, stearic acid, polyethylene glycol, waxes, oils, silica and colloical silica, silicon fluid or talc), disintegrating agents (e.g., potato starch, corn starch and alginic acid), flavouring (e.g. peppermint, oil of wintergreen, fruit flavoring, cherry, grape, bubblegum, and the like), and coloring agents. Carriers may also include coating excipients such as glyceryl monostearate or glyceryl distearate, to delay absorption in the gastrointestinal tract.

Oral liquid preparations, generally in the form of aqueous or oily solutions, suspensions, emulsions or elixirs, may contain conventional additives such as suspending agents, emulsifying agents, non-aqueous agents, preservatives, coloring agents and flavoring agents. Examples of additives for liquid preparations include acacia, almond oil, ethyl alcohol, fractionated coconut oil, gelatin, glucose syrup, glycerin, hydrogenated edible fats, lecithin, methyl cellulose, microcrystalline cellulose, methyl or propyl para-hydroxybenzoate, propylene glycol, sorbitol, or sorbic acid.

For topical use the prodrugs of present invention can also be prepared in suitable forms to be applied to the skin, or mucus membranes of the nose and throat, and can take the form of creams, ointments, nasal drops, liquid sprays or inhalants, lozenges, or throat paints. Such topical formulations further can include chemical compounds such as dimethylsulfoxide (DMSO) to facilitate surface penetration of the active ingredient. For application to the eyes or ears, the prodrugs can be presented in liquid or semi-liquid form formulated in hydrophobic or hydrophilic bases as ointments, creams, lotions, paints or powders. For rectal administration the prodrugs can be administered in the form of suppositories admixed with conventional carriers such as cocoa butter, wax or other glyceride.

V. Use in the Treatment of Neoplasms

In one aspect, the invention relates to a method for inhibiting growth and/or proliferation of cancer cells in a mammal. In another aspect, the invention provides a method for treating neoplasms in a mammal. Mammals include ungulates (e.g. sheeps, goats, cows, horses, pigs), and non-ungulates, including rodents, felines, canines and primates (i.e. human and non-human primates). In a preferred embodiment, the mammal is a human.

The phosphate prodrug of the present invention or its active metabolite may bind to or interact with other cancer-associated proteins and polypeptides, including, without limitation, polypeptides encoded by oncogenes, polypeptides that induce angiogenesis, proteins involved in metastasizing and/or invasive processes, and proteases that regulate apoptosis and the cell cycle. Regardless of the mechanism of action, the phosphate prodrugs of the invention have been demonstrated to convert to Compound 1 in vivo, which metabolite exhibits anti-cancer activity both in vitro and in vivo. Based on these discoveries, applicants have developed methods for treating neoplasms.

As used herein, the terms "neoplasm", "neoplastic condition", "neoplastic disorder", "neoplasia" "cancer," "tumor" and "proliferative disorder" refer to cells having the capacity for autonomous growth, i.e., an abnormal state or condition characterized by rapidly proliferating cell growth which generally results in the formation of a distinct mass that shows partial or total lack of structural organization and functional coordination with normal tissue. The terms are meant to encompass hematopoietic neoplasms (e.g. lymphomas or leukemias) as well as solid neoplasms (e.g. sarcomas or carcinomas), including all types of pre-cancerous and cancerous growths, or oncogenic processes, metastatic tissues or malignantly transformed cells, tissues, or organs, irrespective of histopathologic type or stage of invasiveness. Hematopoietic neoplasms are malignant tumors affecting hematopoietic structures (structures pertaining to the formation of blood cells) and components of the immune system, including leukemias (related to leukocytes (white blood cells) and their precursors in the blood and bone marrow) arising from myeloid, lymphoid or erythroid lineages, and lymphomas (relates to lymphocytes). Solid neoplasms include sarcomas, which are malignant neoplasms that originate from connective tissues such as muscle, cartilage, blood vessels, fibrous tissue, fat or bone. Solid neoplasms also include carcinomas, which are malignant neoplasms arising from epithelial structures (including external epithelia (e.g., skin and linings of the gastrointestinal tract, lungs, and cervix), and internal epithelia that line various glands (e.g., breast, pancreas, thyroid). Examples of neoplasms that are particularly susceptible to treatment by the methods of the invention include leukemia, and hepatocellular cancers, sarcoma, vascular endothelial cancers, breast carcers, central nervous system cancers (e.g. astrocytoma, gliosarcoma, neuroblastoma, oligodendroglioma and glioblastoma), prostate cancers, lung and bronchus cancers, larynx cancers, esophagus cancers, colon cancers, colorectal cancers, gastro-intestinal cancers, melanomas, ovarian and endometrial cancer, renal and bladder cancer, liver cancer, endocrine cancer (e.g. thyroid), and pancreatic cancer.

The phosphate prodrug is administered and converts to its active metabolite, for example, by dephosphorylation via nonspecific phosphatases, which metabolite is brought into contact with or introduced into a cancerous cell or tissue. In general, the methods of the invention for delivering the compositions of the invention in vivo utilize art-recognized protocols for delivering therapeutic agents with the only substantial procedural modification being the substitution of the compound of the present invention for the therapeutic agent in the art-recognized protocols. The route by which the prodrug is administered, as well as the formulation, carrier or vehicle will depend on the location as well as the type of the neoplasm. A wide variety of administration routes can be employed. For example, for a solid neoplasm that is accessible, the prodrug of the invention may be administered by injection directly into the neoplasm. In general, the prodrug may be administered in a manner such that it can be transported systemically through the body of the mammal and thereby reach the neoplasm and distant metastases for example intrathecally, intravenously, intravascularly, intramuscularly or orally. These methods of administration are particularly suitable for the treatment of neoplasms that are not easily accessible within the body (e.g. metastases, brain tumors, hematopoietic neoplasms, etc). Certain mode of administration may be more appropriate for specific types of tumor, for example the prodrug can be administered topically (e.g. for melanoma), rectally (e.g. for colorectal neoplasm) vaginally (e.g. for cervical or vaginal neoplasm), nasally or by inhalation spray (e.g. for lung neoplasm).

The dibenzodiazepinone prodrug is administered in an amount that is sufficient to inhibit the growth or proliferation of a neoplastic cell, or to treat a neoplastic disorder. The term "inhibition" refers to suppression, killing, stasis, or destruction of cancer cells. The inhibition of mammalian cancer cell growth according to this method can be monitored in several ways. To measure the anticancer activity of the prodrug, cancer cells grown in vitro can be treated with the active metabolite and monitored for growth or death relative to the same cells cultured in the absence of the active metabolite. A cessation of growth or a slowing of the growth rate (i.e., the doubling rate), e.g., by 50% or more at 100 micromolar, is indicative of cancer cell inhibition (see Anticancer Drug Development Guide: preclinical screening, clinical trials and approval; B. A. Teicher and P. A. Andrews, ed., 2004, Humana Press, Totowa, N.J.). Alternatively, cancer cell inhibition can be monitored by administering the prodrug to an animal model of the cancer of interest. Examples of experimental non-human animal cancer models are known in the art and described below and in the examples herein. A cessation of tumor growth (i.e., no further increase in size) or a reduction in tumor size (i.e., tumor volume by least a 58% reduction) in animals treated with the prodrug relative to tumors in control animals not treated with the prodrug is indicative of significant tumor growth inhibition (see Anticancer Drug Development Guide: preclinical screening, clinical trials and approval; B. A. Teicher and P. A. Andrews, ed., 2004, Humana Press, Totowa, N.J.).

The term "treatment" refers to the application or administration of a dibenzodiazepinone prodrug of the present invention to a mammal who has a neoplastic disorder, a symptom of a neoplastic disorder or a predisposition toward a neoplastic disorder, with the purpose to cure, heal, alleviate, relieve, alter, ameliorate, improve, or control the disorder, a symptom of disorder, or the predisposition toward disorder. The term "treating" is defined as administering, to a mammal, an amount of a dibenzodiazepinone prodrug sufficient to result in the prevention, reduction or elimination of neoplastic cells in a mammal ("therapeutically effective amount"). The therapeutically effective amount and timing of dosage will be determined on an individual basis and may be based, at least in part, on consideration of the age, body weight, sex, diet and general health of the recipient subject, on the nature and severity of the disease condition, and on previous treatments and other diseases present. Other factors also include the route and frequency of administration, the activity of the administered prodrug and the rate of conversion to its active metabolite, its metabolic stability, length of action and excretion, drug combination, the tolerance of the recipient subject to the compound and the type of neoplasm or proliferative disorder. In one embodiment, a therapeutically effective amount of the prodrug is equivalent to an amount of active metabolite in the range of about 0.5 mg/kg to about 750 mg/kg of body weight of the mammal per day, about 0.5 mg/kg to about 300 mg/kg body weight per day, or about 1 mg/kg to about 50 mg/kg body weight per day. The therapeutically effective doses of the above embodiments may also be expressed in milligrams per square meter ($mg/m^2$), for example, in the case of a human patient. Conversion factors for different mammalian species may be found in:Freireich et al, Quantitative comparison of toxicity of anticancer agents in mouse, rat, dog, monkey and man, Cancer Chemoth. Report, 1966, 50(4): 219-244, incorporated herein by reference in its entirety. When special requirements may be needed (e.g. for children patients), the therapeutically effective doses described above may be outside the ranges stated herein. Such higher or lower doses are within the scope of the present invention.

To monitor the efficacy of tumor treatment in a human, tumor size and/or tumor morphology may be measured before and after initiation of the treatment, and treatment is considered effective if either the tumor size ceases further growth, or if the tumor is reduced in size, e.g., by at least 10% or more (e.g., 20%, 30%, 40%, 50%, 60%, 70%, 80%, 90% or even 100%, that is, the absence of the tumor). Prolongation of survival, time-to-disease progression, partial response and objective response rate are surrogate measures of clinical activity of the investigational agent. Tumor shrinkage is considered to be one treatment-specific response. This system is limited by the requirement that patients have visceral masses that are amenable to accurate measurement. Methods of determining the size of a tumor in vivo vary with the type of tumor, and include, for example, various imaging techniques well known to those in the medical imaging or oncology fields (MRI, CAT, PET, etc.), as well as histological techniques and flow cytometry. For certain types of cancer, evaluation of serum tumor markers are also used to evaluate response (eg prostate-specific antigen (PSA) for prostate cancer, and carcino-embryonic antigen (CEA), for colon cancer). Other methods of monitoring cancer growth include cell counts (e.g. in leukemia) in blood or relief in bone pain (e.g. prostate cancer).

The prodrug of the invention may be administered once daily, or the prodrug may be administered as two, three, four, or more sub-doses at appropriate intervals throughout the day. In that case, the amount contained in each sub-dose must be correspondingly smaller in order to achieve the total daily dosage. The dosage unit can also be compounded for delivery over several days, for example, using a conventional sustained release formulation which provides sustained release of the prodrug over a several day period. In this embodiment, the dosage unit contains a corresponding multiple of the daily dose. The effective dose can be administered either as a single administration event (e.g., a bolus injection) or as a slow injection or infusion, e.g. over 30 minutes to about 14 days. The prodrug may be administered as a treatment, for up to 30 days (e.g. a continuous intravenous infusion, 24 hours per day, for a period of 1 to 28 days). Moreover, treatment of a subject with a therapeutically effective amount of a composition can include a single treatment or a series of treatments (e.g., a four-week treatment repeated 3 times, with a 2 months interval between each treatment). Estimates of effective dosages, toxicities and in vivo half-lives for the prodrugs encompassed by the invention can be made using conventional methodologies or on the basis of in vivo testing using an appropriate animal model.

The prodrug may be administered in conjunction with or in addition to other known anticancer treatments such as surgery, radiotherapy, or other known anticancer compounds or chemotherapeutic agents. Such agents include, but are not limited to, 5-flurouracil, mitomycin C, methotrexate, hydroxyurea, nitrosoureas (e.g., BCNU, CCNU), cyclophosphamide, procarbazine, dacarbazine, thiotepa, atreptozocine, temozolomide, enzastaurin, erlotinib, mitoxantrone, anthracyclins (Epirubicin and Doxurubicin), CPT-11, camptothecin and derivatives thereof, etoposide, navelbine, vinblastine, vincristine, pregnasone, platinum compounds such as carboplatin and cisplatin, taxanes such as taxol and taxotere; hormone therapies such as tamoxifen and antiestrogens; antibodies to receptors, such as herceptin and Iressa; aromatase inhibitors, progestational agents and LHRH analogs; biological response modifiers such as IL2 and interferons; multidrug reversing agents such as the cyclosporin analog PSC 833. (For more examples, see: *The Merck Index*, 12$^{th}$ edition (1996)).

Toxicity and therapeutic efficacy of prodrugs can be determined by standard pharmaceutical procedures in experimental animals. Therapeutic efficacy is determined in animal models as described above and in the examples herein. Toxicity studies are done to determine the lethal dose for 10% of tested animals (LD10). Animals are treated at the maximum tolerated dose (MTD): the highest dose not producing mortality or greater than 20% body weight loss. The effective dose (ED) is related to the MTD in a given tumor model to determine the therapeutic index of the prodrug. A therapeutic index (MTD/ED) close to 1.0 has been found to be acceptable for some chemotherapeutic drugs, a preferred therapeutic index for classical chemotherapeutic drugs is 1.25 or higher.

The data obtained from cell culture assays and animal studies can be used in formulating a range of dosages for use in humans. The dosage of compositions of the invention will generally be within a range of circulating concentrations that include the MTD. The dosage may vary within this range depending upon the dosage form employed and the route of administration utilized. For any prodrug used in the method of the invention, the therapeutically effective dose can be estimated initially from cell culture assays using its active metabolite, and in vivo animal models using the prodrug. A dose may be formulated in animal models to achieve a circulating plasma concentration range of the active metabolite (e.g. Compound 1). Such information can be used to more accurately determine useful doses in humans. Levels in plasma may be measured, for example, by HPLC.

Animal models to determine in vivo antitumor efficacy of a prodrug are generally carried out in mice. Either murine tumor cells are inoculated subcutaneously into the hind flank of mice from the same species (syngeneic models) or human tumor cells are inoculated subcutaneously into the hind flank of severe combined immune deficient (SCID) mice or other immune deficient mice (nude mice) (xenograft models).

Advances in mouse genetics have generated a number of mouse models for the study of various human diseases including cancer. The MMHCC (Mouse models of Human Cancer Consortium) web page (emice.nci.nih.gov), sponsored by the National Cancer Institute, provides disease-site-specific compendium of known cancer models, and has links to the searchable Cancer Models Database (cancermodels.nci.nih.gov ), as well as the NCI-MMHCC mouse repository. Mouse repositories can also be found at: The Jackson Laboratory, Charles River Laboratories, Taconic, Harlan, Mutant Mouse Regional Resource Centers (MMRRC) National Network and at the European Mouse Mutant Archive. Such models may be used for in vivo testing of the prodrug compounds, as well as for determining a therapeutically effective dose.

In addition to the phosphate prodrugs of the invention, pharmaceutically acceptable salts and/or solvates of said prodrugs may also be employed in compositions to treat or prevent the above-identified disorders.

EXAMPLES

Unless otherwise noted, all reagents were purchased from Sigma Chemical Co. (St. Louis, Mo.), Aldrich, or J. T. Baker USA.

All NMR spectra were collected in deuterated solvent on a Varian 500™ Spectrometer ($^1$H NMR at 500 MHz, $^{13}$C NMR at 125 MHz). Unless otherwise indicated, UV and mass spectra were collected by Waters 2690™ HPLC using a photodiode array detector (PDA, 210-400 nm) coupled to a Waters Micromass™ ZQ™ mass detector.

Unless otherwise indicated, all numbers expressing quantities of ingredients, properties such as molecular weight, reaction conditions, molar equivalents (eq), solubilities, plasma concentrations, GI$_{50}$ and so forth used in the specification and claims are to be understood as being modified in all instances by the term "about". Accordingly, unless indicated to the contrary, the numerical parameters set forth in the present specification and attached claims are approximations. At the very least, and not as an attempt to limit the application of the doctrine of equivalents to the scope of the claims, each numerical parameter should at least be construed in light of the number of significant figures and by applying ordinary rounding techniques. Not withstanding that the numerical ranges and parameters setting forth the broad scope of the invention are approximations, the numerical values set in the examples, Tables and Figures are reported as precisely as possible. Any numerical values may inherently contain certain errors resulting from variations in experiments, testing measurements, statistical analyses and such.

In the following section, examples describe in detail the chemical synthesis of representative compounds of the present invention. The procedures are illustrations, and the invention should not be construed as being limited by chemical reactions and conditions they express. No attempt has been made to optimize the yields obtained in these reactions, and it would be obvious to one skilled in the art that variations in reaction times, temperature, solvent and/or reagents could increase the yields.

In addition, the materials, methods, and examples, including in vitro and in vivo efficacy, in vitro metabolism by liver extract, pharmacokinetics, solubility and toxicity are illustrative only and not intended to be limiting. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control.

Example 1

Production of Compound 1 By Fermentation

Compound 1, which was used to prepare the prodrugs, was isolated from the fermentation broth of either strains of *Micromonospora* [S01]046 or 046-ECO11, respectively having IDAC 231203-01 and 070303-01 accession numbers (International Depository Authority of Canada (IDAC), Bureau of Microbiology, Health Canada, 1015 Arlington Street, Winnipeg, Manitoba, Canada, R3E 3R2). Compound 1 was produced and isolated according to the procedures described in the PCT Patent Application published as WO 2004/065591, incorporated herein by reference in its entirety.

Example 2

Phosphorylation Reactions—Triphosphates

The phosphorylation of Compound 1 to produce Compounds 2, 3, 6 and 7 was accomplished using a variation of the procedure described in Silverberg et al (1996), *Tet. Lett.*, vol 37, 771-774.

a) Synthesis and Structural Elucidation of Compound 2

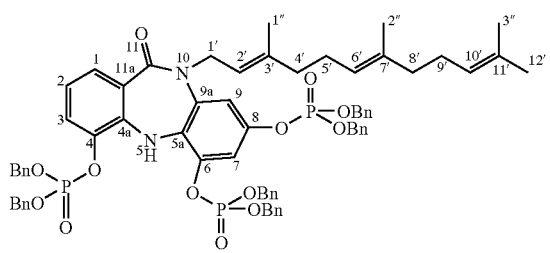

$C_{70}H_{73}N_2O_{13}P_3$
Mol. Wt.: 1242.43

Compound 2, namely 10-farnesyl-4,6,8-tri(bisbenzyloxyphosphoryloxy)-5,10-dihydro-dibenzo[b,e][1,4]diazepin-11-one, was prepared and identified as follows:

Preparation:

Compound 1 (100.0 mg) was dissolved in acetonitrile ($CH_3CN$, 1.4 mL) and stirred at room temperature. Carbon tetrachloride (104 μL), N,N-diisopropyl ethylamine (227 μL), 4-dimethylaminopyridine (DMAP, 2.63 mg) and dibenzylphosphite (265 μL) were successively added to the Compound 1 solution, and the reaction mixture was stirred at room temperature for one hour. The reaction was monitored by LC/MS. The reaction mixture was subjected to semi-preparative HPLC (Waters with 2996 PDA (photodiode array detector)) on Nova-Pack™ 6 μm C18 25×200 mm column (20 mL/min, $H_2O/CH_3CN$, linear gradient 50:50-0:100, 0-6 min; isocratic 0:100, 6-20 min), to provide Compound 2 (140 mg), eluting at 14.7 min.

Structural elucidation:

The calculated molecular weight for the major isotope (1242.43) and formula ($C_{70}H_{73}N_2O_{13}P_3$) of Compound 2 was confirmed by mass spectral analysis: positive ionization gave an $(M+H)^+$ molecular ion of 1244.6. The structure was further elucidated by 1- and 2-dimension NMR spectral analysis. Proton NMR spectral analysis is shown in Table 1. Signals were assigned based on Compound 1 structure knowledge.

b) Synthesis and Structural Elucidation of Compound 16-free Acid

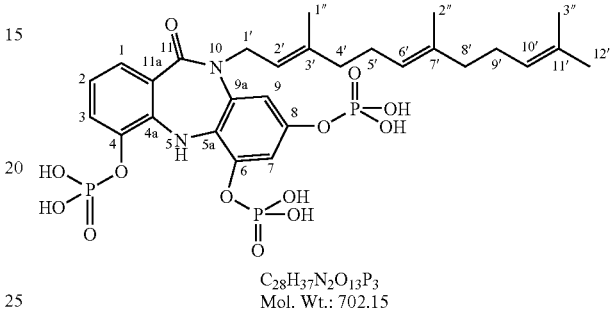

$C_{28}H_{37}N_2O_{13}P_3$
Mol. Wt.: 702.15

Compound 16-free acid: 10-farnesyl-4,6,8-triphosphonooxy-5-ethyl-5,10-dihydro-dibenzo[b,e][1,4]diazepin-11-one was prepared and identified as follows:

Preparation:

Compound 2 (100 mg) was dissolved in methanol (MeOH, 5.0 mL) and 1% Pd/C (50 mg) was added to the mixture. The mixture was stirred under hydrogen atmosphere for 20 min and filtered. The filtrate was concentrated in vacuo. Pure Compound 16-free acid (25 mg) was isolated by preparative HPLC using the HPLC apparatus and column described in (a) (20 mL/min, $H_2O/CH_3CN$, linear gradient 80:20-50:50, 0-12 min; linear gradient 50:50-0:100, 12-13 min), eluting at 7.0 min.

Structural elucidation:

The calculated molecular weight of the major isotope (702.15) and formula ($C_{28}H_{37}N_2O_{13}P_3$) of Compound 16-free acid was confirmed by mass spectral analysis: negative ionization gave an $(M-H)^-$ molecular ion of 701.0 and positive ionization gave an $(M+H)^+$ molecular ion of 703.2. Proton NMR signals were assigned as shown in Table 1.

c) Synthesis and Structural Elucidation of Compound 16-hexaammonium

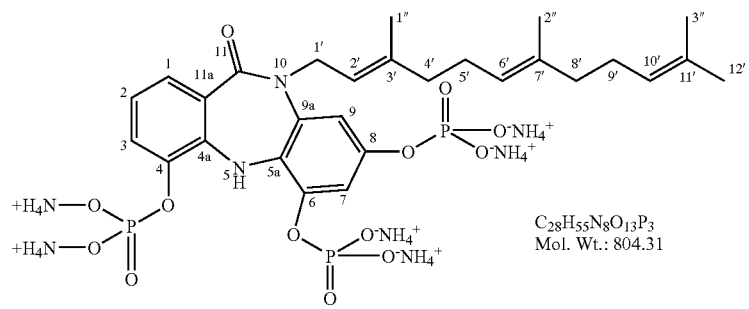

$C_{28}H_{55}N_8O_{13}P_3$
Mol. Wt.: 804.31

Compound 16-hexaammonium: 10-farnesyl-4,6,8-triphosphonooxy-5-ethyl-5,10-dihydro-dibenzo[b,e][1,4]diazepin-11-one hexaammonium salt was prepared as follows:

Preparation:

A diluted ammonium hydroxide solution was directly added to the filtrate obtained in (b). The solution was concentrated in vacuo until a white precipitate appeared. The white precipitate was separated by filtration. The white precipitate was subjected to the HPLC system and column described in (a) (20 mL/min, H$_2$O(10 mM NH$_4$OAc)/CH$_3$CN, linear gradient 80:20-50:50, 0-12 min; linear gradient 50:50-0:100, 12-13 min), to provide Compound 16-hexaammonium (20 mg) eluting at 7.8 min.

Structural elucidation:

The calculated molecular weight of the major isotope (702.15) and formula (C$_{28}$H$_{37}$N$_2$O$_{13}$P$_3$) of the molecular ion of Compound 16-hexaammonium (without its ammonium counterions) was confirmed by mass spectral analysis: negative ionization gave an (M−H)$^-$ molecular ion of 701.0 and positive ionization gave an (M+H)$^+$ molecular ion of 703.2. Proton NMR signals were assigned as shown in Table 1.

d) Synthesis and Structural Elucidation of Compound 16-hexasodium

Compound 16-hexasodium: 10-farnesyl-4,6,8-tris(phosphonooxy)-5-ethyl-5,10-dihydro-dibenzo[b,e][1,4]diazepin-11-one hexasodium salt was prepared as follows:

Preparation:

A saturated methanol solution of Compound 16-hexaammonium from (c) (30.0 mg) was mixed with a saturated methanol solution of sodium iodide. The precipitate (26 mg) formed was filtered and washed with methanol.

Structural elucidation:

The calculated molecular weight of the major isotope (702.15) and formula (C$_{28}$H$_{37}$N$_2$O$_{13}$P$_3$) of the molecular ion of Compound 16-hexasodium (without its sodium counterions) was confirmed by mass spectral analysis: negative ionization gave an (M−H)$^-$ molecular ion of 701.0 and positive ionization gave an (M+H)$^+$ molecular ion of 703.1. Proton NMR signals were assigned as shown in Table 1.

TABLE 1

$^1$H NMR ($\delta_H$, ppm) Data in MeOH-D$_4$ of Compound 2 and Compounds 16-free acid, 16-hexaammonium and 16-hexasodium

| Assignment | 2 | 16 | 16 (NH$_4^+$)$_6$ | 16 (Na$^+$)$_6$ | Group |
|---|---|---|---|---|---|
| 1 | 7.60 | 7.51 | 7.64 | 7.61 | CH |
| 2 | 6.98 | 7.02 | 6.91 | 6.86 | CH |
| 3 | 7.36 | 7.47 | 7.36 | 7.30 | CH |
| 4-OR$^a$ | * | N/A | N/A | N/A | Bn (14H)$^a$ |
| 5-NH | 6.79 | 6.15 | 6.29 | 7.35 | NH |
| 6-OR$^a$ | * | N/A | N/A | N/A | Bn (14H)$^a$ |
| 7 | 7.02 | 7.17 | 7.35 | 6.85 | CH |
| 8-OR$^a$ | * | N/A | N/A | N/A | Bn (14H)$^a$ |
| 9 | 6.88 | 7.06 | 6.93 | 6.95 | CH |
| 1' | 4.44 | 4.61 | 4.61 | 4.60 | CH$_2$ |
| 2' | 5.24 | 5.39 | 5.38 | 5.38 | CH |
| 4' | 2.00 | 2.10 | 2.04 | 2.06 | CH$_2$ |
| 5' | 2.01 | 2.10 | 2.06 | 2.09 | CH$_2$ |
| 6' | 5.04 | 5.12 | 5.12 | 5.13 | CH |
| 8' | 1.91 | 1.96 | 1.97 | 1.97 | CH$_2$ |
| 9' | 1.94 | 2.10 | 2.02 | 2.02 | CH$_2$ |
| 10' | 5.04 | 5.07 | 5.10 | 5.09 | CH |
| 12' | 1.61 | 1.65 | 1.67 | 1.67 | CH$_3$ |
| 1" | 1.64 | 1.76 | 1.75 | 1.74 | CH$_3$ |
| 2" | 1.54 | 1.61 | 1.60 | 1.61 | CH$_3$ |
| 3" | 1.52 | 1.56 | 1.61 | 1.60 | CH$_3$ |

N/A: not applicable, group not present in the molecule
* signals of benzyl groups were poorly resolved multiplets at δ 7.29 to 7.19 ppm (CH Aryl) and δ 5.12 to 5.04 ppm (CH$_2$).
$^a$R is PO(OBn)$_2$ in Compound 2 and PO(OM)$_2$ in Compounds 16-free acid (M = H), 16-hexaammonium (M = NH$_4$) and 16-hexasodium (M = Na)

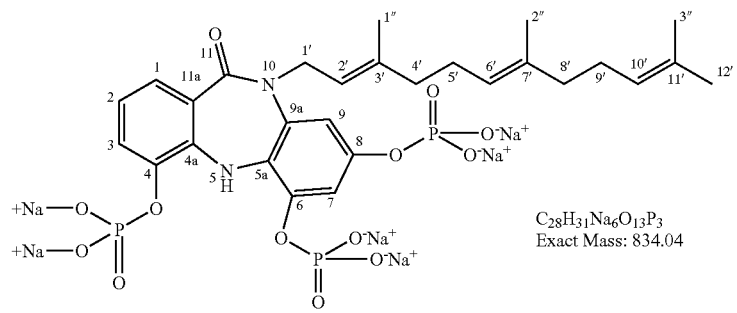

C$_{28}$H$_{31}$Na$_6$O$_{13}$P$_3$
Exact Mass: 834.04 e) Synthesis and Structural Elucidation of Compound 9-trisodium

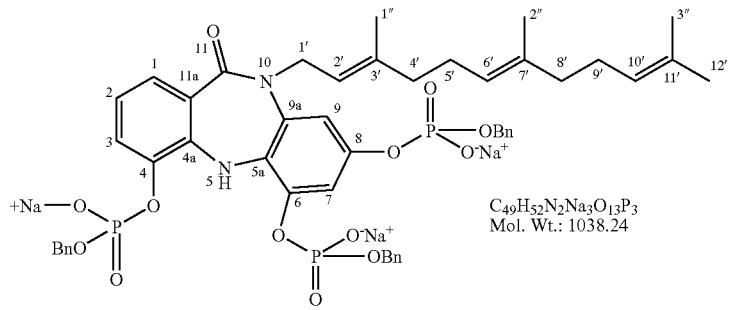

Compound 9-trisodium, namely 10-farnesyl-4,6,8-tri(benzyloxyhydroxyphosphoryloxy)-5,10-dihydro-dibenzo[b,e][1,4]diazepin-11-one trisodium salt, was prepared and identified as follows:

Preparation:

Compound 2 (15 mg) was dissolved in acetonitrile ($CH_3CN$, 3.0 mL), treated with sodium iodide (25 mg) and the reaction was stirred at room temperature overnight. The reaction mixture was subjected to preparative HPLC (Waters with 2996 PDA) on ACE™ 5 μm C18 21×250 mm column (20 mL/min, $H_2O/CH_3CN$, linear gradient 80:20-30:70, 0-8 min; linear gradient 30:70-0:100, 8-18 min), to provide Compound 9-trisodium (5 mg), eluting at 6.0 min.

Structural elucidation:

The calculated molecular weight of the major isotope (972.29) and formula ($C_{49}H_{55}N_2O_{13}P_3$) of the molecular ion of Compound 9-trisodium (without its sodium counterions) was confirmed by mass spectral analysis: negative ionization gave an $(M-H)^-$ molecular ion of 971.0 and positive ionization gave an $(M+H)^+$ molecular ion of 973.0. Proton NMR spectral analysis is shown in Table 2.

f) Synthesis and Structural Elucidation of Compound 9-triammonium

Compound 9-triammonium, namely 10-farnesyl-4,6,8-tri(benzyloxyhydroxy phosphoryloxy)-5,10-dihydro-dibenzo[b,e][1,4]diazepin-11-one triammonium salt, was prepared and identified as follows:

Preparation:

Compound 9-trisodium (25 mg) was dissolved in methanol (MeOH, 5 mL) and treated with an excess of $NH_4OAc$ (100 mg), and the reaction stirred at room temperature for 15 min. The reaction mixture was subjected to semi-preparative HPLC using Nova-Pack™ 5 μm C18 21×250 mm column (20 mL/min, $H_2O$(10 mM $NH_4OAc$)/$CH_3CN$ gradient 80:20-0:100, 0-15 min), to provide Compound 9-triamonium (20 mg), eluting at 8.4 min.

Structural elucidation:

The calculated molecular weight of the major isotope (972.29) and formula ($C_{49}H_{55}N_2O_{13}P_3$) of the molecular ion of Compound 9-triammonium (without its ammonium counterions) was confirmed by mass spectral analysis: negative ionization gave an $(M-H)^-$ molecular ion of 971.3 and

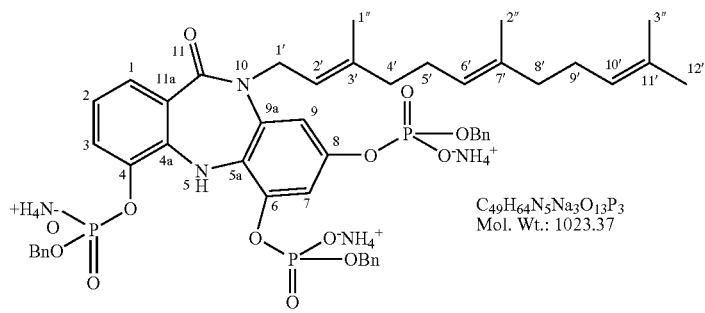

positive ionization gave an (M+H)+ molecular ion of 973.5. Proton NMR spectral analysis is shown in Table 2.

TABLE 2

¹H NMR (δ_H, ppm) Data of Compounds 9-trisodium and 9-triammonium in MeOH-D₄

| Assignment | 9 (Na⁺)₃ | 9 (NH₄⁺)₃ | Group |
|---|---|---|---|
| 1 | 7.55 | 7.53 | CH |
| 2 | 6.88 | 6.90 | CH |
| 3 | 7.41 | 7.44 | CH |
| 4-OR[a] | * | * | Bn(7H) |
| 6-OR[a] | * | * | Bn(7H) |
| 7 | 7.24 | 7.36 | CH |
| 8-OR[a] | * | * | Bn(7H) |
| 9 | 7.04 | 6.93 | CH |
| 1' | 4.53 | 4.50 | CH₂ |
| 2' | 5.30 | 5.30 | CH |
| 4' | 2.04 | 2.04 | CH₂ |
| 5' | 2.06 | 2.04 | CH₂ |
| 6' | 5.09 | 5.09 | CH |
| 8' | 1.91 | 1.94 | CH₂ |
| 9' | 2.03 | 2.04 | CH₂ |
| 10' | 5.06 | 5.06 | CH |
| 12' | 1.67 | 1.66 | CH₃ |
| 1'' | 1.67 | 1.67 | CH₃ |
| 2'' | 1.59 | 1.58 | CH₃ |
| 3'' | 1.57 | 1.57 | CH₃ |

* signals of benzyl groups at δ 7.30-7.17 ppm (CH Aryl) and δ 5.03-4.92 ppm (CH₂) for both compounds.
[a] R is PO(O⁻Na⁺)(OBn) in Compound 9-trisodium and PO(O⁻NH₄⁺)(OBn) in Compound 9-triammonium.

Example 3

Phosphorylation Reactions—Monophosphates a) Synthesis and Structural Elucidation of Compounds 6 and 7

Compound 6, namely 10-farnesyl-4-(bis-benzyloxyphosphoryloxy)-6,8-dihydroxy-5,10-dihydro-dibenzo[b,e][1,4]diazepin-11-one, and

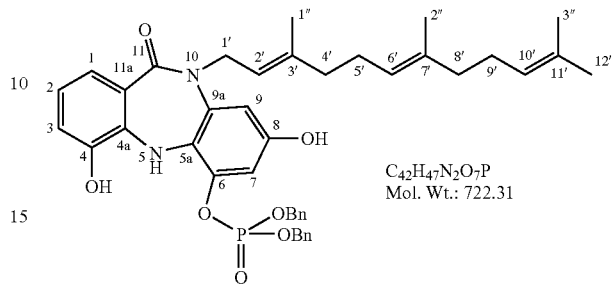

Compound 7, namely 10-farnesyl-4,8-dihydroxy-6-(bisbenzyloxyphosphoryloxy)-5,10-dihydro-dibenzo[b,e][1,4]diazepin-11-one, were prepared and identified as follows:

Preparation:

Compound 1 (1.38 g) was dissolved in acetonitrile (CH₃CN, 15 mL) and stirred at room temperature. Carbon tetrachloride (1.5 mL), N,N-diisopropyl ethylamine (4.2 mL), 4-dimethylamiopyridine (DMAP, 40 mg) and dibenzylphosphite (660 μL) were successively added to the Compound 1 solution, and the reaction mixture was stirred at room temperature for an hour. The reaction was monitored by LC/MS. All possible phosphates (monophosphates 6, 7 and 8, diphosphates 3, 4 and 5 and triphosphate 2) were detected. The reaction mixture was subjected to preparative HPLC (Waters with 2996 PDA detector) using a YMC-ODS AQ™ 5μ column (20 mL/min, H₂O(10 mM NH₄OAc)/CH₃CN, 30:70 isocratic 0-40 min; linear gradient 30:70-0:100, 40-45 min), to provide Compounds 6 (75 mg) and 7 (100 mg), eluting respectively at 35.5 and 36.0 min. Compound 8 was also detected by LC/MS in small quantity but was not isolated.

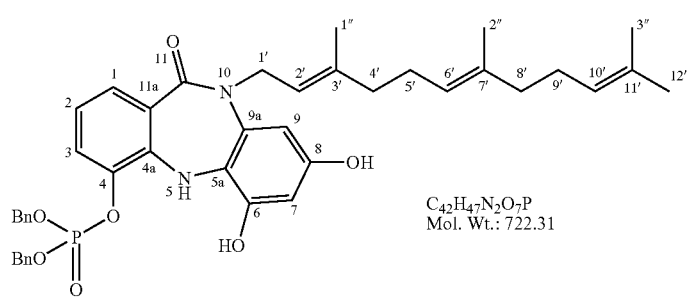

Structural elucidation:

The calculated molecular weight of the major isotope (722.31) and formula ($C_{42}H_{47}N_2O_7P$) of Compound 6 was confirmed by mass spectral analysis: negative ionization gave an $(M-H)^-$ molecular ion of 721.3 and positive ionization gave an $(M+H)^+$ molecular ion of 723.4. Proton NMR signals were assigned as shown in Table 3 below.

The calculated molecular weight of the major isotope (722.31) and formula ($C_{42}H_{47}N_2O_7P$) of Compound 7 was confirmed by mass spectral analysis: negative ionization gave an $(M-H)^-$ molecular ion of 721.3 and positive ionization gave an $(M+H)^+$ molecular ion of 723.4. Proton NMR signals were assigned as shown in Table 3 below.

b) Synthesis and Structural Elucidation of Compounds 20-diammonium and 21-diammonium gradient 80:20-40:60, 0-6 min; linear gradient 40:60-0:100, 6-7 min), eluting respectively at 5.0 and 5.3 min.

Structural elucidation:

The calculated molecular weight of the major isotope (542.22) and formula ($C_{28}H_{35}N_2O_7P$) of the molecular ion of Compound 20-diammonium (without its ammonium counterions) was confirmed by mass spectral analysis: negative ionization gave an $(M-H)^-$ molecular ion of 541.1 and positive ionization gave an $(M+H)^+$ molecular ion of 543.1. Proton NMR signals were assigned as shown in Table 3.

The calculated molecular weight of the major isotope (542.22) and formula ($C_{28}H_{35}N_2O_7P$) of the molecular ion of Compound 21-diammonium (without its ammonium counterions) was confirmed by mass spectral analysis: negative ionization gave an $(M-H)^-$ molecular ion of 541.1 and

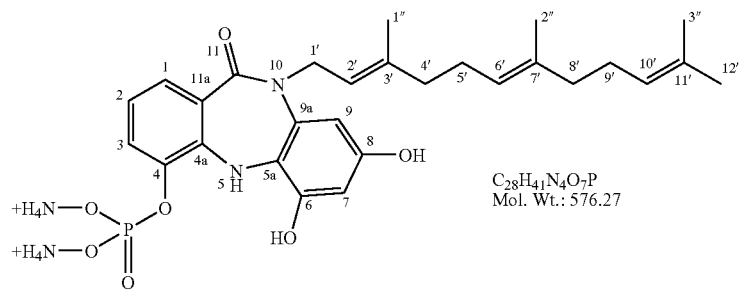

Compound 20-diammonium, namely 6,8-dihydroxy-10-farnesyl-4-phosphonooxy-5,10-dihydro-dibenzo[b,e][1,4]diazepin-11-one diammonium salt, and

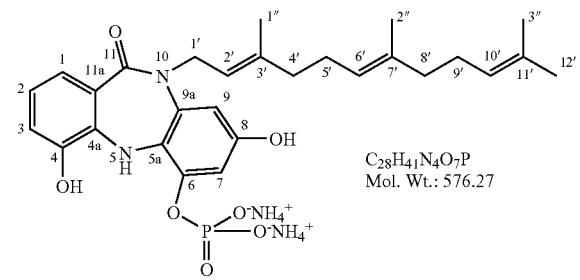

Compound 21-diammonium, namely 4,8-dihydroxy-10-farnesyl-6-phosphonooxy-5,10-dihydro-dibenzo[b,e][1,4]diazepin-11-one diammonium salt, were prepared and identified as follows:

Preparation:

The mono-bisbenzylphosphate (Compound 6 or 7, 100 mg) was dissolved in methanol (MeOH, 10.0 mL) and 5% Pd/C (20 mg) was added to the mixture. The mixture was stirred under hydrogen atmosphere for 10 min. The reaction mixture was filtered and concentrated in vacuo. Compound 20-diammonium (25 mg, by reacting Compound 6) or Compound 21-diammonium (25 mg, by reacting Compound 7) was isolated by preparative HPLC (Waters Auto-Prep) on a Symmetry™ C-18 6μ column (39 mL/min with at column dilution (1 mL/min), $H_2O$(10 mM $NH_4OAc$)/$CH_3CN$, linear positive ionization gave an $(M+H)^+$ molecular ion of 543.1. Proton NMR signals were assigned as shown in Table 3.

TABLE 3

$^1$H NMR ($\delta_H$, ppm) Data of Compounds 6,7,20-diammonium and 21-diammonium in MeOH-$D_4$

| Assignment | 6 | 7 | 20 $(NH_4^+)_2$ | 21 $(NH_4^+)_2$ | Group |
|---|---|---|---|---|---|
| 1 | 7.52 | 7.21 | 7.50 | 7.18 | CH |
| 2 | 6.87 | 6.83 | 6.86 | 6.78 | CH |
| 3 | 7.32 | 6.89 | 7.37 | 6.89 | CH |
| 4-OR[a] | 7.32, 5.22 | N/A | N/A | N/A | Bn (14H)[a] |
| 6-OR[b] | N/A | 7.32, 5.20 | N/A | N/A | Bn (14H)[b] |
| 7 | 6.31 | 6.72 | 6.31 | 6.86 | CH |
| 9 | 6.26 | 6.64 | 6.26 | 6.50 | CH |
| 1' | 4.57 | 4.57 | 4.54 | 4.53 | $CH_2$ |
| 2' | 5.36 | 5.37 | 5.39 | 5.43 | CH |
| 4' | 2.04 | 2.04 | 2.06 | 2.06 | $CH_2$ |
| 5' | 2.09 | 2.09 | 2.11 | 2.14 | $CH_2$ |
| 6' | 5.09 | 5.09 | 5.12 | 5.15 | CH |
| 8' | 1.96 | 1.95 | 1.97 | 1.98 | $CH_2$ |
| 9' | 2.04 | 2.04 | 2.06 | 2.06 | $CH_2$ |
| 10' | 5.07 | 5.07 | 5.09 | 5.09 | CH |
| 12' | 1.64 | 1.64 | 1.66 | 1.66 | $CH_3$ |
| 1" | 1.73 | 1.74 | 1.74 | 1.75 | $CH_3$ |
| 2" | 1.59 | 1.60 | 1.61 | 1.63 | $CH_3$ |
| 3" | 1.55 | 1.54 | 1.57 | 1.57 | $CH_3$ |

N/A: not applicable, group not present in the molecule
[a]R is $PO(OBn)_2$ in Compound 6, $PO(O^-NH_4^+)_2$ in Compound 20-diammonium and H in Compounds 7 and 21-diammonium.
[b]R is $PO(OBn)_2$ in Compound 7, $PO(O^-NH_4^+)_2$ in Compound 21-diammonium and H in Compounds 6 and 20-diammonium.

Example 4

Phosphorylation Reactions—Diphosphates a) Synthesis and Structural Elucidation of Compounds 3, 4 and 5

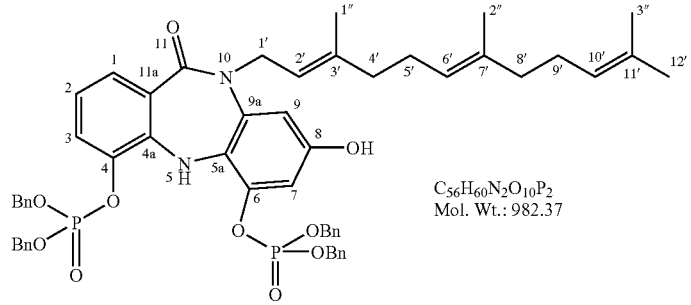

Compound 3, namely 10-farnesyl-4,6-di(bis-benzyloxyphosphoryloxy)-8-hydroxy-5,10-dihydro-dibenzo[b,e][1,4]diazepin-11-one,

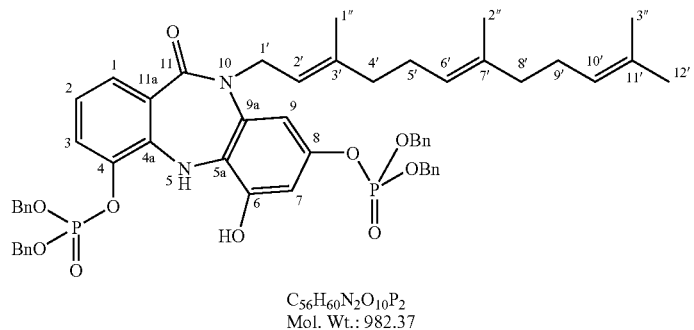

Compound 4, namely 10-farnesyl-4,8-di(bis-benzyloxyphosphoryloxy)-6-hydroxy-5,10-dihydro-dibenzo[b,e][1,4]diazepin-11-one,

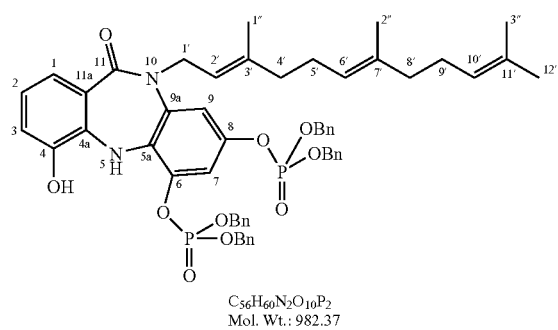

Compound 5, namely 10-farnesyl-6,8-di(bis-benzyloxyphosphoryloxy)-4-hydroxy-5,10-dihydro-dibenzo[b,e][1,4]diazepin-11-one, were prepared and identified as follows:

Preparation:

Compound 1 (230.0 mg) was dissolved in acetonitrile ($CH_3CN$, 10 mL) and stirred at room temperature. Carbon tetrachloride (259 μL), N,N-diisopropyl ethylamine (700 μL), 4-dimethylamiopyridine (DMAP, 6.5 mg) and dibenzylphosphite (100 μL) were successively added to the solution, and the reaction mixture was stirred at room temperature for one hour. The reaction mixture was subjected to preparative HPLC (Waters with 2996 PDA) on a XTeera™ C-18 10 μm 20×150 mm column (20 mL/min, $H_2O$(10 mM $NH_4OAc$)/$CH_3CN$; linear gradient 30:70-80:20, 0-5 min; 80:20-0:100, 5-10 min isocratic 0:100, 10:14 min), to provide major product Compound 3 (24.7 mg, RT 10.4 min), Compound 4 and 5 in mixture (30.0 mg, RT 10.9 min).

Structural elucidation:

The calculated molecular weight for the major isotope (982.37) and formula ($C_{56}H_{60}N_2O_{10}P_2$) of Compound 3 was confirmed by mass spectral analysis: negative ionization gave an $(M-H)^-$ molecular ion of 981.6 and positive ionization gave an (M+H) molecular ion of 983.8. Proton NMR spectral analysis is shown in Table 4.

The calculated molecular weight for the major isotope (982.37) and formula ($C_{56}H_{60}N_2O_{10}P_2$) of Compound 4 was confirmed by mass spectral analysis: negative ionization gave an $(M-H)^-$ molecular ion of 981.6 and positive ionization gave an $(M+H)^+$ molecular ion of 983.8. Proton NMR spectral analysis is shown in Table 4.

The calculated molecular weight for the major isotope (982.37) and formula ($C_{56}H_{60}N_2O_{10}P_2$) of Compound 5 was confirmed by mass spectral analysis: negative ionization gave an $(M-H)^-$ molecular ion of 981.6 and positive ionization gave an $(M+H)^+$ molecular ion of 983.8. Proton NMR spectral analysis is shown in Table 4.

TABLE 4

$^1$H NMR ($\delta_H$, ppm) Data of Compounds 3, 4 and 5 in MeOH-$D_4$

| Assignment | 3 | 4 | 5 | Group |
|---|---|---|---|---|
| 1 | 7.55 | 7.55 | a | CH |
| 2 | 6.93 | a | a | CH |
| 3 | 7.26 | 7.48 | a | CH[a] |
| 4-OR[b] | * | ** | N/A | Bn(14H)[b] |
| 5-NH | 6.63 | — | — | NH |
| 6-OR[c] | * | N/A | *** | Bn(14H)[c] |
| 7 | 6.60 | 6.73 | 6.94 | CH |
| 8-OR[d] | N/A | ** | *** | Bn(14H)[d] |
| 9 | 6.65 | 6.59 | 6.86 | CH |
| 1' | 4.58 | 4.57 | 4.57 | $CH_2$ |
| 2' | 5.37 | 5.38 | 5.34 | CH |
| 4' | 2.03 | 2.04 | 2.04 | $CH_2$ |
| 5' | 2.08 | 2.04 | 2.04 | $CH_2$ |
| 6' | 5.09** | a | a | CH |
| 8' | 1.95 | 1.94 | 1.94 | $CH_2$ |
| 9' | 2.03 | 2.04 | 2.04 | $CH_2$ |
| 10' | 5.05** | a | a | CH |
| 12' | 1.63 | 1.63 | 1.63 | $CH_3$ |
| 1" | 1.74 | 1.74 | 1.74 | $CH_3$ |
| 2" | 1.58 | 1.60 | 1.58 | $CH_3$ |
| 3" | 1.54 | 1.55 | 1.55 | $CH_3$ |

N/A: not applicable, group not present in the molecule
* benzyl groups as poorly resolved multiplets at δ 7.31-7.21 ppm (CHAr) and δ 5.10-5.05 ppm ($CH_2$).
** benzyl groups as poorly resolved multiplets at δ 7.35-7.24 ppm (CHAr) and δ 5.11-5.06 ppm ($CH_2$).
*** benzyl groups as poorly resolved multiplets at δ 7.35-7.24 ppm (CHAr) and δ 5.11-5.06 ppm ($CH_2$).
[a] overlapping with signals of the benzyl groups
[b] R is $PO(OBn)_2$ in Compounds 3 and 4, H in Compound 5.
[c] R is $PO(OBn)_2$ in Compounds 3 and 5, H in Compound 4.
[d] R is $PO(OBn)_2$ in Compounds 4 and 5, H in Compound 3.

b) Synthesis and Structural Elucidation of Compound 17-tetraammonium

Compound 17-tetraammonium, namely 10-farnesyl-4,6-diphosphonooxy-8-hydroxy-5,10-dihydro-dibenzo[b,e][1,4]diazepin-11-one tetraammonium salt, was prepared and identified as follows:

Preparation:

Compound 3 (24.7 mg) was dissolved in methanol (MeOH, 3.0 mL) and 1% Pd/C (10 mg) was added to the solution. The reaction mixture was stirred under hydrogen atmosphere for 5 min. The reaction mixture was filtered and concentrated in vacuo. Compound 17-tetraammonium (4.0 mg) was isolated by preparative HPLC (Waters with 2996 PDA) using an ACE™ C-18 5μ column 21×250 mm (20 mL/min, $H_2O$(10 mM $NH_4OAc$)/$CH_3CN$, gradient 80:20-0:100, 0-20 min; 0:100 isocratic, 20-24 min), eluting at 9.3 min.

Structural elucidation:

The calculated molecular weight of the major isotope (622.18) and formula ($C_{28}H_{36}N_2O_{10}P_2$) of the molecular ion of Compound 17-tetraammonium (without its ammonium counterions) was confirmed by mass spectral analysis: negative ionization gave an $(M-H)^-$ molecular ion of 620.9 and positive ionization gave an $(M+H)^+$ molecular ion of 623.0. Proton NMR signals were assigned as shown in Table 5.

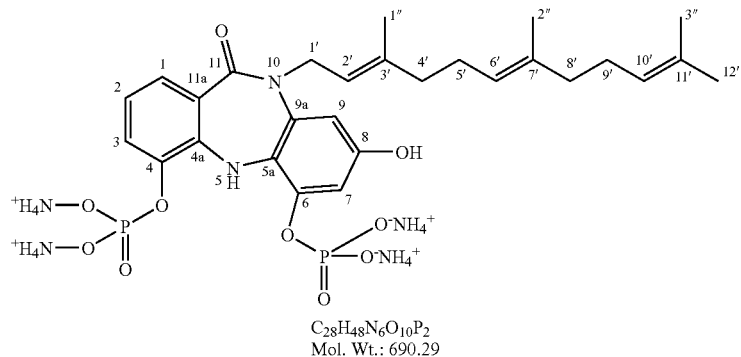

$C_{28}H_{48}N_6O_{10}P_2$
Mol. Wt.: 690.29 c) Synthesis and Structural Elucidation of Compound 18-tetraammonium

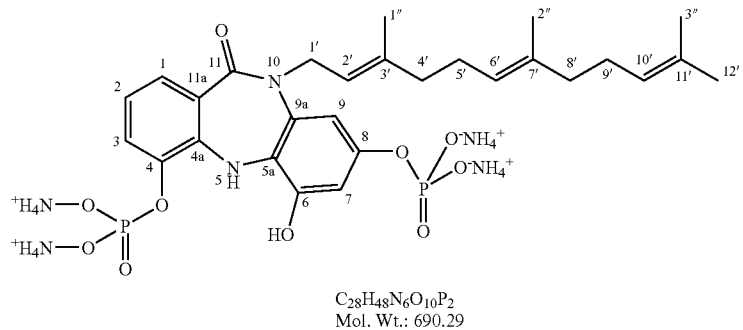

$C_{28}H_{48}N_6O_{10}P_2$
Mol. Wt.: 690.29

Compound 18-tetraammonium, namely 10-farnesyl-4,8-diphosphonooxy-6-hydroxy-5,10-dihydro-dibenzo[b,e][1,4]diazepin-11-one tetraammonium salt, was prepared and identified as follows:

Preparation:

Compound 4 and 5 (30.0 mg) was dissolved in methanol (MeOH, 3.0 mL) and 1% Pd/C (10 mg) was added to the solution. The reaction mixture was stirred under hydrogen atmosphere for 5 min. The reaction mixture was filtered and concentrated in vacuo. Compound 18-tetraammonium (3.2 mg) was isolated by preparative HPLC (Waters with 2996 PDA) using an YMC QC™ C-18 5μ column 21×250 mm (20 mL/min, $H_2O$(10 mM $NH_4OAc$)/$CH_3CN$, gradient 95:5-0:100, 0-20 min; 0:100 isocratic, 20-24 min), eluting at 8.5 min.

Structural elucidation:

The calculated molecular weight of the major isotope (622.18) and formula ($C_{28}H_{36}N_2O_{10}P_2$) of the molecular ion of Compound 18-tetraammonium (without its ammonium counterions) was confirmed by mass spectral analysis: negative ionization gave an $(M-H)^-$ molecular ion of 621.2 and positive ionization gave an $(M+H)^+$ molecular ion of 623.4. Proton NMR signals were assigned as shown in Table 5.

d) Synthesis and Structural Elucidation of Compound 19-tetraammonium

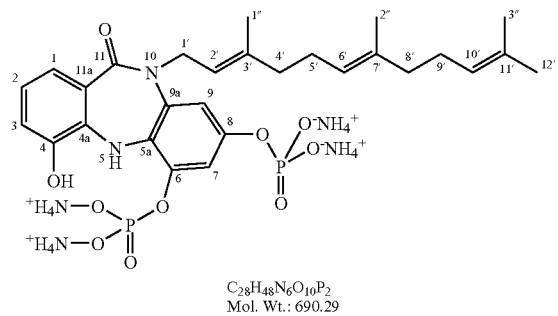

$C_{28}H_{48}N_6O_{10}P_2$
Mol. Wt.: 690.29

Compound 19-tetraammonium, namely 10-farnesyl-6,8-diphosphonooxy-4-hydroxy-5,10-dihydro-dibenzo[b,e][1,4]diazepin-11-one tetraammonium salt, was prepared and identified as follows:

Preparation:

Compounds 4 and 5 in mixture (30 mg) were dissolved in methanol (MeOH, 30 mL) and 1% Pd/C (10 mg) was added to the solution. The reaction mixture was stirred under hydrogen atmosphere for 5 min. The reaction mixture was filtered and concentrated in vacuo. Compound 19-tetraammonium (20 mg) was isolated by preparative HPLC (Waters with 2996 PDA) using an YMC QC™ C-18 5μ column 21×250 mm (20 mL/min, $H_2O$(10 mM $NH_4OAc$)/$CH_3CN$, gradient 95:5-0:100, 0-20 min; 0:100 isocratic, 20-24 min), eluting at 8.0 min.

Structural Elucidation:

The calculated molecular weight of the major isotope (622.18) and formula ($C_{28}H_{36}N_2O_{10}P_2$) of the molecular ion of Compound 19-tetraammonium (without its ammonium counterions) was confirmed by mass spectral analysis: negative ionization gave an $(M-H)^-$ molecular ion of 621.2 and positive ionization gave an $(M+H)^+$ molecular ion of 623.4. Proton NMR signals were assigned as shown in Table 5.

TABLE 5

$^1$H NMR ($\delta_H$, ppm) Data of the tetraammonium salts of Compounds 17, 18 and 19 in MeOH-$D_4$

| Assignment | 17 $(NH_4^+)_4$ | 18 $(NH_4^+)_4$ | 19 $(NH_4^+)_4$ | Group |
|---|---|---|---|---|
| 1 | 7.61 | 7.61 | 7.19 | CH |
| 2 | 6.89 | 6.87 | 6.80 | CH |
| 3 | 7.35 | 7.38 | 6.91 | CH |
| 7 | 6.96 | 6.73 | 7.22 | CH |
| 9 | 6.48 | 6.70 | 6.09 | CH |
| 1' | 4.56 | 4.58 | 4.58 | $CH_2$ |
| 2' | 5.41 | 5.38 | 5.39 | CH |
| 4' | 2.06 | 2.06 | 2.06 | $CH_2$ |
| 5' | 2.13 | 2.08 | 2.10 | $CH_2$ |
| 6' | 5.14 | 5.11 | 5.13 | CH |
| 8' | 1.98 | 1.97 | 1.97 | $CH_2$ |
| 9' | 2.06 | 2.01 | 2.03 | $CH_2$ |
| 10' | 5.09 | 5.09 | 5.09 | CH |
| 12' | 1.66 | 1.67 | 1.67 | $CH_3$ |
| 1" | 1.75 | 1.74 | 1.75 | $CH_3$ |
| 2" | 1.62 | 1.61 | 1.61 | $CH_3$ |
| 3" | 1.58 | 1.59 | 1.59 | $CH_3$ |

Example 5

Solubilty in Water

Solubilities in water of exemplified Compounds 9-trisodium, 9-triammonium, 16-free acid, 16-hexaammonium, 16-hexasodium, 17-tetraammonium, 20-diammonium, and 21-diammonium were compared to the solubility of Compound 1 in water and the results are shown in Table 6.

TABLE 6

Compared Aqueous Solubility

| Compound | Solubility (g/mL) |
|---|---|
| 1 | 0.005 |
| 9 (Na$^+$)$_3$ | >40 |
| 9 (NH$_4{}^+$)$_3$ | >40 |
| 16 | >40 |
| 16 (NH$_4{}^+$)$_6$ | >200 |
| 16 (Na$^+$)$_6$ | >200 |
| 17 (NH$_4{}^+$)$_4$ | >20 |
| 20 (NH$_4{}^+$)$_2$ | 5.0 |
| 21 (NH$_4{}^+$)$_2$ | 5.0 |

The results of Table 6 shows that all phosphate prodrugs tested exhibited a high increase in water solubility. In fact, the proportion of aqueous solubility of the phosphates tested ranged from 1000 times to more than 40000 times the aqueous solubility of Compound 1. As such, the prodrugs have the required solubility to be formulated in an aqueous vehicle (may require a buffer) with no or little use of solubilizers, which generally exhibit some level of toxicity.

Example 6

In Vitro Profiling of the Compounds of the Invention

In vitro Anticancer Activity of the Compounds of Formula I Against Four Cell Lines:

In vitro cytotoxic activities of exemplified Compounds are shown in Table 7. Compounds were tested in four cell lines: HT-29 (colorectal carcinoma), SF268 (CNS), MDA-MB-231 (mammary gland adenocarcinoma) and PC-3 (prostate adenocarcinoma). Procedure used for the tests is described below.

TABLE 7

In vitro Cytotoxic Activities (GI$_{50}$ µM)

| Compound | HT-29 | SF-268 | PC-3 | MDA-MB-231 | Average |
|---|---|---|---|---|---|
| 1 | 11.23 | 1.96 | 1.95 | 1.79 | 4.23 |
| 2 | >30 | >30 | >30 | >30 | >30 |
| 9 (NH$_4{}^+$)$_3$ | >30 | >30 | >30 | >30 | >30 |
| 16 (free) | >30 | >30 | >30 | >30 | >30 |
| 16 (NH$_4{}^+$)$_6$ | >30 | >30 | >30 | >30 | >30 |
| 20 (NH$_4{}^+$)$_2$ | >30 | >30 | >30 | >30 | >30 |
| 21 (NH$_4{}^+$)$_2$ | >30 | >30 | >30 | >30 | >30 |
| A[a] | 9.33 | 1.95 | 1.20 | 2.79 | 3.82 |
| B[b] | 12.61 | 1.88 | 1.44 | 2.48 | 4.60 |
| C[c] | 16.02 | 5.79 | 5.35 | 7.72 | 8.72 |
| D[d] | 13.01 | 2.02 | 1.35 | 1.55 | 4.48 |

[a] A is the 4,6,8-triacetate of Compound 1
[b] B is the 4,6-diacetate of Compound 1
[c] C is the 4,8-diacetate of Compound 1
[d] D is the 6,8-diacetate of Compound 1

In vitro activities of phosphate Compound 2 and ammonium salts of phosphate Compounds 9, 16, 20 and 21 were compared with in vitro activities of Compound 1 and acetates A to D (respectively Compounds 12, 10, 11 and 9 of US patent publication 2006/0079509). None of the phosphate Compounds 2 and 16, and ammonium salts of Compounds 9, 16, 20 and 21 exhibited in vitro anticancer activity at 30 µM. This showed that the phosphate prodrugs were relatively stable in the experiment conditions, and were inactive unless they were enzymatically cleaved, for example by non specific phosphatases, to liberate their active metabolite Compound 1. Also, since phosphates were highly polar, they did not cross cell membranes easily without being first converted to Compound 1.

All acetates described in Table 7 exhibited in vitro anticancer activity comparable to Compound 1. Although acetates behave as prodrugs (they liberate the parent active molecule), they would certainly be less stable than the phosphates under formulation conditions. In fact, the acetates were cleaved in methanol or under in vitro testing conditions. Furthermore, they would not provide a more soluble precursor for Compound 1.

Procedure:

In vitro cytotoxic activities (GI$_{50}$) of Compounds 2 and 16, and ammonium salts of Compounds 9, 16, 20 and 21 were assessed by determining the concentration of drug resulting in 50% growth inhibition using a propidium iodide (PI) dye indicator according to the following method.

Two 96-well plates were seeded in duplicate with each cell line at the appropriate inoculation density (HT29: 3,000; SF268: 3,000; PC-3: 3,000; and MDA-MB-231: 7,500 cells) and according to the technical data sheet of each cell line (rows A-G, 75 µL of media per well). Row H was filled with medium only (150 µL, negative control-medium). The plates were incubated at appropriate temperature and CO$_2$ concentration for 24 hrs.

Test Compounds were prepared as 15× stock solutions in appropriate medium and corresponding to 450, 45, 0.45, 0.045, and 0.0045 µM (prepared the day of the experiment). An aliquot of each was diluted 7.5-fold in appropriate test medium to give a set of six 2× concentration solutions (60, 6, 0.6, 0.06, 0.006, and 0.0006 µM). A 75 µL aliquot of each concentration was added to each corresponding well (rows A to F) of the second plate. Row G was filled with 75 µL of medium/0.6% DMSO (negative control-cells). The second plate was incubated at appropriate temperature and CO$_2$ concentration for 96 hrs.

First Plate: PI (30 µL, 50 µg/mL) was added to each well of the first plate without removing the culture medium. The plate was centrifuged (Sorvall Legend-RT, swinging bucket) at 3500 rpm/10 min. Fluorescence intensity (Thermo, Varioskan, $\lambda_{ex}$: 530 nm; $\lambda_{em}$: 620 nm) was measured to give the first measurement, dead cells (DC at T$_0$; before freezing). Two round of Freeze (−80° C.)/Thaw (37° C.) were done. Fluorescence intensity was determined to give the second measure, total cells (TC at T$_0$; after freeze/thaw)

Second plate was processed as the first one, except there were three rounds of freeze/thaw instead of two. First measurement gave the treated dead cells value (TDC), and the second measurement gave the treated total cells value (TTC). Both values were collected for each treated well and control (CTC and CDC).

Each value (DC, TC, TDC, TTC, CTC and CDC) was corrected by removing the background value (medium only) to give the value (FU$_{DC(T=0)}$, FU$_{TC(T=0)}$, FU$_{TDC}$, FU$_{TTC}$, FU$_{CTC}$ and FU$_{CDC}$) used in the calculation of the T/C (%) (Treated/Control) for each concentration. T/C (%) for each concentration is calculated using the following formula:

$$T/C(\%) = \frac{(FU_{TTC} - FU_{TDC}) - (FU_{TC(T=0)} - FU_{DC(T=0)}) \times 100}{(FU_{CTC} - FU_{CDC}) - (FU_{TC(T=0)} - FU_{DC(T=0)})}$$

The GI$_{50}$ value emphasizes the correction for the cell count at time zero for cell survival. The T/C values are transposed in a graph to determine $GI_{50}$ values, the concentration at which the T/C is 50%.

Example 7

Conversion to Compound 1 By Rat Liver Homogenate a) Example procedure:

Compounds 16-hexaammonium and 9-triammonium were tested for conversion to Compound 1 in rat liver homogenates. The aim of this test was to determine if the phosphate prodrugs were cleaved by phosphatases present in the liver.

Procedure:

The following were prepared:

Buffer A: 242 mg of Tris base (Ultra Pure) and 745 mg of sodium chloride were weighed, transferred in a 100-mL volumetric flask and diluted with purified water. The pH was adjusted to 7.4 with concentrated hydrochloric acid and the volume was made up to 100 mL with water.

Buffer B: 0.294 g of sodium and 0.4 g of L-ascorbic acid were dissolved in 30 mL of water and the pH was adjusted to 3.0 using concentrated formic acid. The solution was transferred into a 100-mL volumetric flask, diluted with methanol to 100 mL and well mixed. Buffer B was stored at 4° C., protected from light for a maximum of 2 weeks.

Rat liver (3 g from Sprague Dawley rats) was weighed into a centrifuge tube and 12 mL of Buffer A was added, representing a 1:4 tissue/buffer ratio, which were homogenized for at least 30 seconds at ambient temperature.

Stock solutions of test article, control and internal standards were prepared as shown in Table 8 by diluting the compound in the appropriate solvent.

TABLE 8

Stock solutions for rat liver homogenate

| Stock no | Compound | Quantity (mg) | Solvent | Volume (mL) | Concentration |
|---|---|---|---|---|---|
| B | 16 $(NH_4^+)_6$ | 2.30 | 0.9% saline | 5.0 | 460 µg/mL |
| C | 9 $(NH_4^+)_3$ | 2.17 | 0.9% saline | 5.0 | 434 µg/mL |
| D | 1 | 2.13 | Buffer B | 5.0 | 426 µg/mL |
| E | 1 (N-CD$_3$) IS[a] | 1.0 | Buffer B | 10.0 | 100 µg/mL |
| F | 1 (N-CD$_3$) IS[a] | 50 µL[b] | CH$_3$CN | 25.0 | 200 ng/mL |

[a]IS: internal standard; Cnd 1(N-CD$_3$) is Compound 98 of US PGPub 2006/0079509
[b]50 µL of Stock solution E.

Working solutions were prepared by dilution of the stock solutions, giving working solutions labeled WB-1 to WB-3 (230000, 115000 and 57500 ng/mL of Compound 16-hexaammonium in 0.9% saline), working solutions labeled WC-1 to WC-8 (217000, 108500, 54250, 27125, 13563, 6781, 3391, 1695 and 848 ng/mL of Compound 9-triammonium in 0.9% saline), working solutions labeled WD-1 to WD-9 (213000, 106500, 53250, 26625, 13313, 6656, 3328, 1664 and 832 ng/mL of Compound 1 in acetonitrile).

Liver homogenate (180 µL) was transferred into Eppendorf™ tubes (polypropylene, size 1.8 mL). Tubes for Blank, 0 min, 30 min, 1 h, 2 h, 3 h, 4 h and 5 h for each concentration of compound to be tested. Blank tubes were prepared by adding 200 µL of homogenate per tube. Each tube (except blank tubes) was spiked with 20 µL of each working solution, and vortexed to reach drug concentrations of about 5 and 20 µg/mL for test article WB-1, WB-3, and WC-1, WC-3.

Immediately after vortexing, the 0 min samples (for calibration) were extracted with extraction Methods A and B (see below). The remaining tubes were incubated at 37° C. for the prescribed length of time.

Calibration curves were done for Compound 1 using LC-MS/MS Method A, and Compound 9-triammonium using LC-MS/MS method B.

Extraction methods:

Method A was used to monitor the prodrug/Compound 1 ratio (without using an internal standard). A volume of 400 µL of 8.3% perchloric acid in acetonitrile was added to the homogenate and the mixture vortexed for 30 sec. The mixture was allowed to stand for 10 minutes at room temperature. It was then centrifuged at 13000 RPM for 5 minutes at 4° C. The supernatant was tested by LC-MS/MS (Method B).

Method B was used to quantify Compound 1 present in the rat liver homogenate (with an internal standard (IS)). A volume of 800 µL of acetonitrile containing IS 200 ng/mL (Stock F) was added to the homogenate and the mixture vortexed for 30 sec. The mixture was allowed to stand at room temperature for 10 minutes, and was centrifuged at 13000 RPM for 5 minutes at 4° C. The supernatant was tested by LC-MS/MS (Method A).

LC-MS/MS methods:

Both LC methods were accomplished using the same HPLC system (Agilent Technologies 1100 with Binary pump and autosampler, and an Agilent 1100 Autosampler needle wash to avoid contamination of the needle. Both MS/MS method were done using a MDS Sciex™ MS system under positive electrospray ionization.

LC Method A (short method) was done using 20 µL of test solution on a Phenomenex™ Luna Phenyl-Hexyl, 3µ (4.6× 30 mm id) and a divert pump flow rate of 1.0 ml/min using the conditions described in Table 9.

TABLE 9

LC Method A conditions

| Time | Flow rate | % H$_2$O[a] | % CH$_3$CN[a] |
|---|---|---|---|
| 0.00 | 1.0 | 50 | 50 |
| 0.75 | 1.0 | 50 | 50 |
| 2.00 | 1.0 | 0 | 100 |
| 4.50 | 1.0 | 0 | 100 |
| 4.60 | 1.5 | 50 | 50 |
| 5.50 | 1.5 | 50 | 50 |
| 6.00 | 1.0 | 50 | 50 |

[a]Both H$_2$O and CH$_3$CN containing 0.2% formic acid.

Multiple Reaction Monitoring (MRM) was used as scan type in Method A MS/MS. The ions monitored were those of Compound 1 (463.3 and 271.2, RT 2.8 min) and the internal standard Compound 1(N-CD$_3$) (480.5 and 288.0, RT 3.1 min).

LC Method B (long method) was done using 20 µL of test solution on a Waters Symmetry™ C-18, 3.5µ (3.0×100 mm id) and a divert pump flow rate of 1.0 ml/min using the conditions described in Table 10.

TABLE 10

LC Method B conditions

| Time | Flow rate | % H₂O[a] | % CH₃CN |
|---|---|---|---|
| 0 | 1.0 | 80 | 20 |
| 25 | 1.0 | 5 | 95 |
| 25.10 | 1.0 | 0 | 100 |
| 29 | 1.0 | 0 | 100 |
| 32 | 1.0 | 80 | 20 |
| 37 | 1.0 | 80 | 20 |

[a]$H_2O$ containing 10 mM ammonium acetate.

Enhanced Product Ion (EPI) was used as scan type in Method B MS/MS. The ions monitored were those of Compound 1 (463.3, RT 20-21 min), Compound 9triammonium (973.3, RT 7.8-8.5 min) and 16-hexaammonium (703.15, RT 5.0-5.5 min).

Results:

The results obtained for Compounds 16-hexaammonium and 9-triammonium at 5 μmL and 20 μg/mL in homogenate are summarized in Table 11.

TABLE 11

Conversion of Compounds 16-hexaammonium and 9-triammonium to Compound 1 in liver homogenate

| Initial Cpnd[a] | Initial Conc. | Cpnd Test[b] | Concentration (ng/mL) vs Time of Incubation | | | | | | |
|---|---|---|---|---|---|---|---|---|---|
| | | | 0 min | 0.5 h | 1 h | 2 h | 3 h | 4 h | 5 h |
| 16 ($NH_4^+$)₆ | 5 μg/mL | 1 | <LOD | 12.7 | 14.5 | 74.1 | 113 | 258 | 267 |
| 16 ($NH_4^+$)₆ | 20 μg/mL | 1 | <LOD | 34.9 | 91.4 | 391 | 719 | 1060 | 1330 |
| 9 ($NH_4^+$)₃ | 5 μg/mL | 1 | <LOD | <LOD | <LOD | 11.1 | 26.6 | 50.6 | 75.6 |
| 9 ($NH_4^+$)₃ | 5 μg/mL | 9 | 1840 | 2040 | 2570 | 856 | 544 | <LOD | <LOD |
| 9 ($NH_4^+$)₃ | 20 μg/mL | 1 | <LOD | <LOD | <LOD | 35 | 114 | 202 | 322 |
| 9 ($NH_4^+$)₃ | 20 μg/mL | 9 | 13300 | 14600 | 9030 | 2970 | 1530 | 1080 | 948 |

[a]Initial Cpnd: Compound added to the liver homogenate.
[b]Cpnd Test: Compound for which the concentration was analyzed in the LC-MS/MS method and for which the results are tabulated.
<LOD: below the limit of detection.

b) Results:

Ammonium salts of Compounds 9, 16, 20 and 21, and sodium salts of Compounds 9 and 16, were tested and compared to Compound 1 using the procedure of (a) at a concentration of 10 μg/mL in homogenate and their conversion to Compound 1 are summarized in FIG. 1.

The results obtained in the above experiments showed that most phosphates are converted to Compound 1 in rat liver extracts at different rates. They were showed to convert to active Compound 1 through the action of liver enzymes, such as phosphatases, which further supports their application as prodrugs. Ammonium salts of monophosphate prodrug Compounds 20 and 21 showed the higher rate of conversion to Compound 1 in rat liver homogenates, giving levels of Compound 1 higher than Compound 1 itself, which starts metabolizing.

Figure 2:
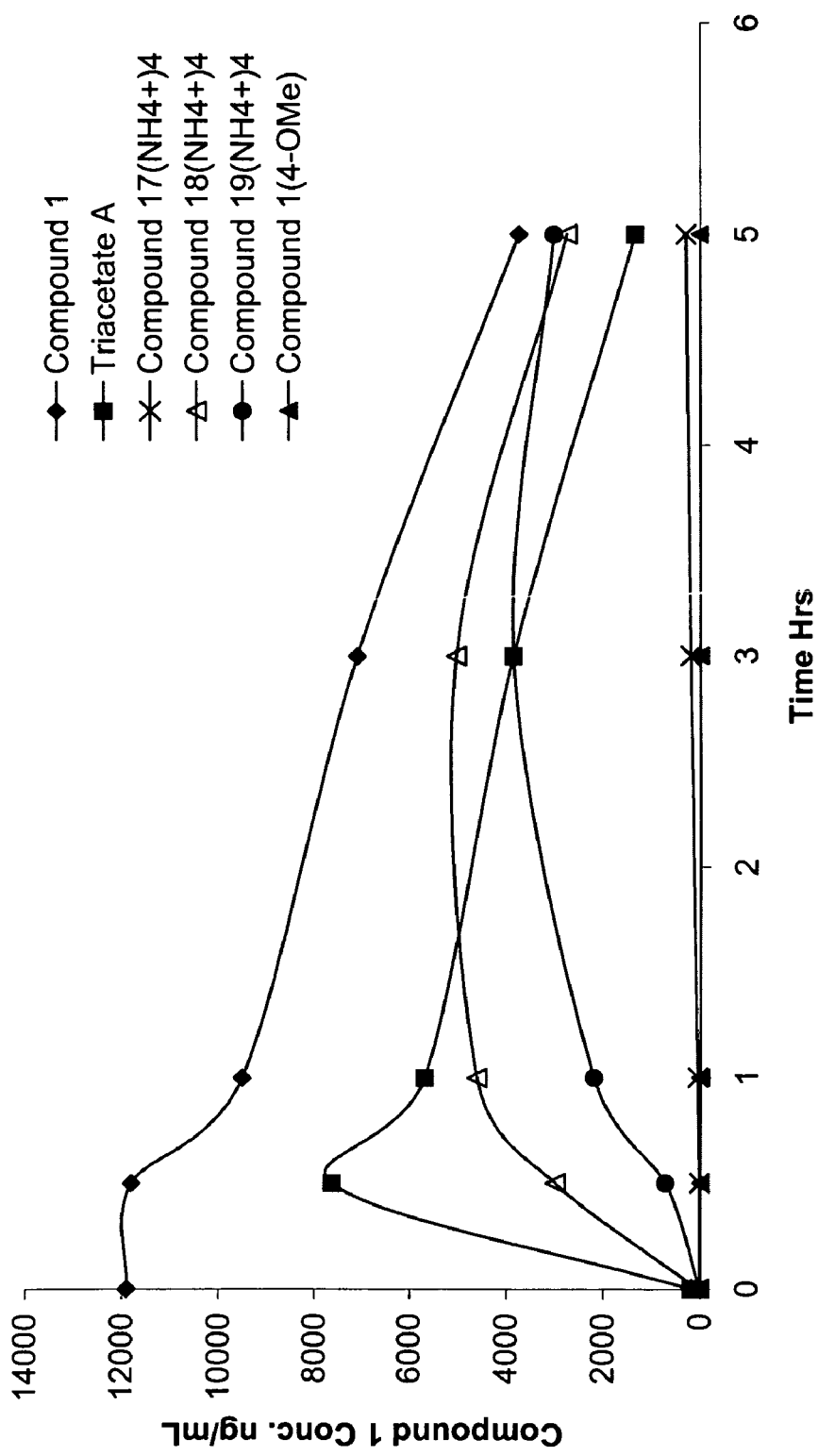
FIG. 2: shows levels of Compound 1 when Compounds 17-tetraammonium, 18-tetraammonium and 19-tetraammonium are converted in vitro to Compound 1 using rat liver homogenate. The results were compared to Compound 1, and two derivatives of Compound 1, the 4,6,8-triacetate and the 4-methoxy analogs.

Ammonium salts of the diphosphates Compounds 17, 18 and 19 were also tested and compared to Triacetate A, Compound 1(4-OMe) (respectively Compounds 12 and 4 of US patent publication 2006/0079509) and Compound 1 using the procedure exemplified in (a) at a concentration of 10 μg/mL in homogenate and their conversion to Compound 1 are summarized in FIG. 2.

The results showed that all three diphosphates are converted to Compound 1 at different rates. Compound 17-tetraammonium had the lowest rate of conversion of the three but was still converted to Compound 1. The triacetate, as expected from previous experiments was converted very rapidly to Compound 1, and was then metabolized at the same rate as Compound 1 was as control. The 4-O-methyl analog of Compound 1 did not convert to Compound 1, which indicates that the methyl ether would not behave as a prodrug.

Example 8

Pharmacokinetic Profiles

Compounds 16-hexaammonium, 16-hexasodium and 20-diammonium were tested for conversion into Compound 1 in Sprague-Dawley rats (Charles River Canada Inc., Montreal, Canada).

(a) Compound 16-hexaammonium

Compound 16-hexaammonium was dissolved in 0.9% saline at a final concentration of 10.5 mg/mL. Compound 16-hexaammonium was administered intravenously (i.v.) to the assigned animals at a dose of 52.5 mg/kg (volume of 5 mL/kg) (2 subsets of 3 rats each), corresponding to 30 mg/kg of Compound 1 per dose. Blood samples were collected from the orbital sinus on various occasions, alternating bleeds for each of the two subsets (2 min, 15 min, 1 h, 4 h, 24 h for subset A; 5 min, 30 min, 2 h, 8 h for subset B). Each blood sample (approximately 0.5 mL) was collected into microtainer tubes containing anticoagulant $K_2$EDTA. The samples were centrifuged at a temperature ranging from about 2 to about 8° C. for 10 minutes at 1500 g (RCF). A volume of 25 μL of 4% w/v L-aqueous acid was added to a volume of 225 μL of rat plasma in a clean tube, and the samples were mixed by inversion.

The plasma samples were tested by liquid chromatography-tandem mass spectrometry (LC-MS/MS) using multi reaction monitoring (MRM) for Compound 1 concentration. Standard curve ranged from about 25 to about 10000 ng/mL with limit of quantitation (LOQ) of about 25 ng/mL and limit of detection (LOD) of about 10 ng/mL. LOQ and LOD values were determined according to the concentration range used in the experiment, using a MDS Sciex API 2000™ Q-Trap™. Mean concentration values and standard deviation (SD) were calculated at each timepoints of the pharmacokinetic study (n=3 animals/timepoint).

Figure 3:
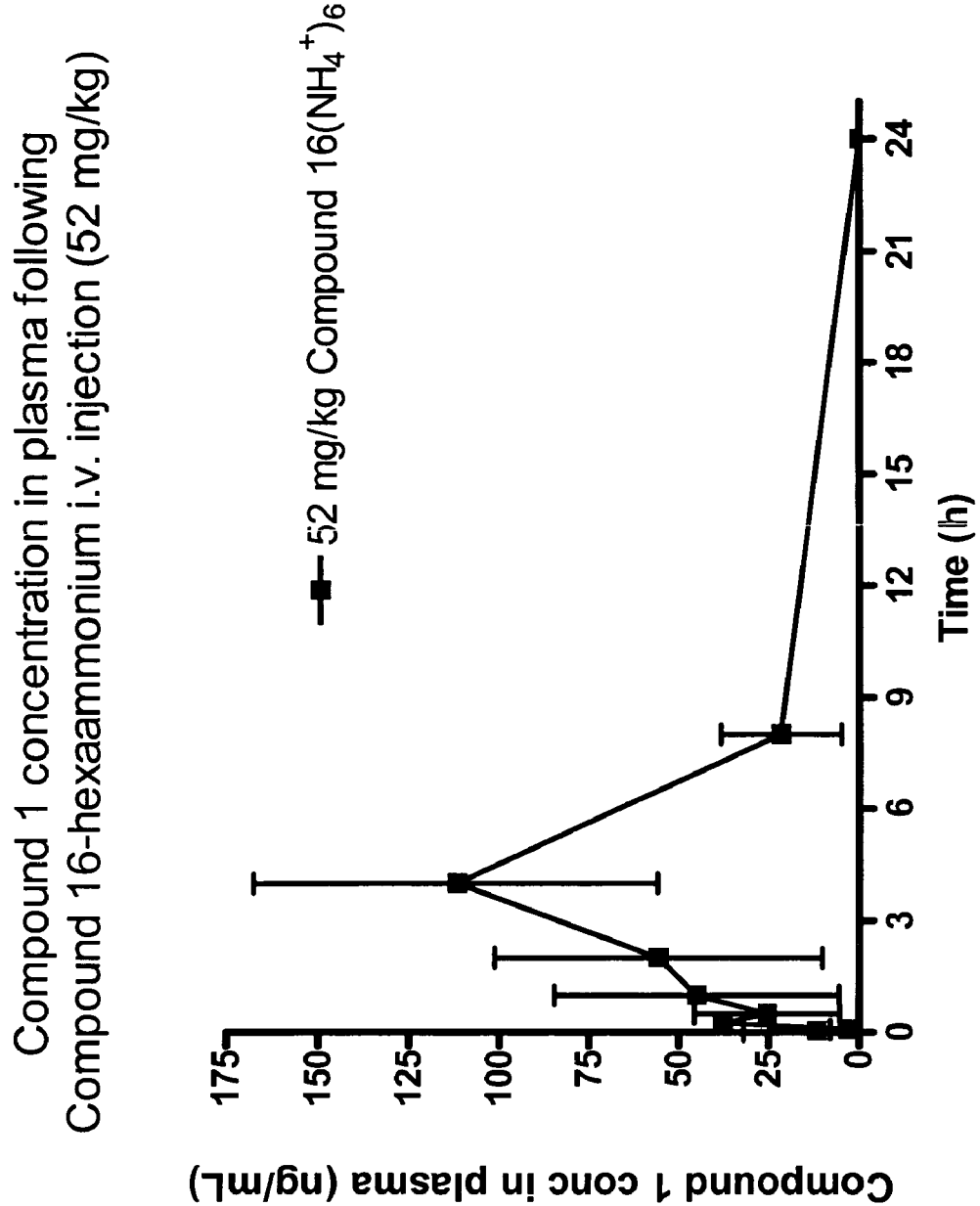
FIG. 3: shows mean (±SD) plasma concentrations of Compound 1 following bolus intravenous (i.v.) administration of Compound 16-hexaammonium (52 mg/kg) in rats.
Figure 4:
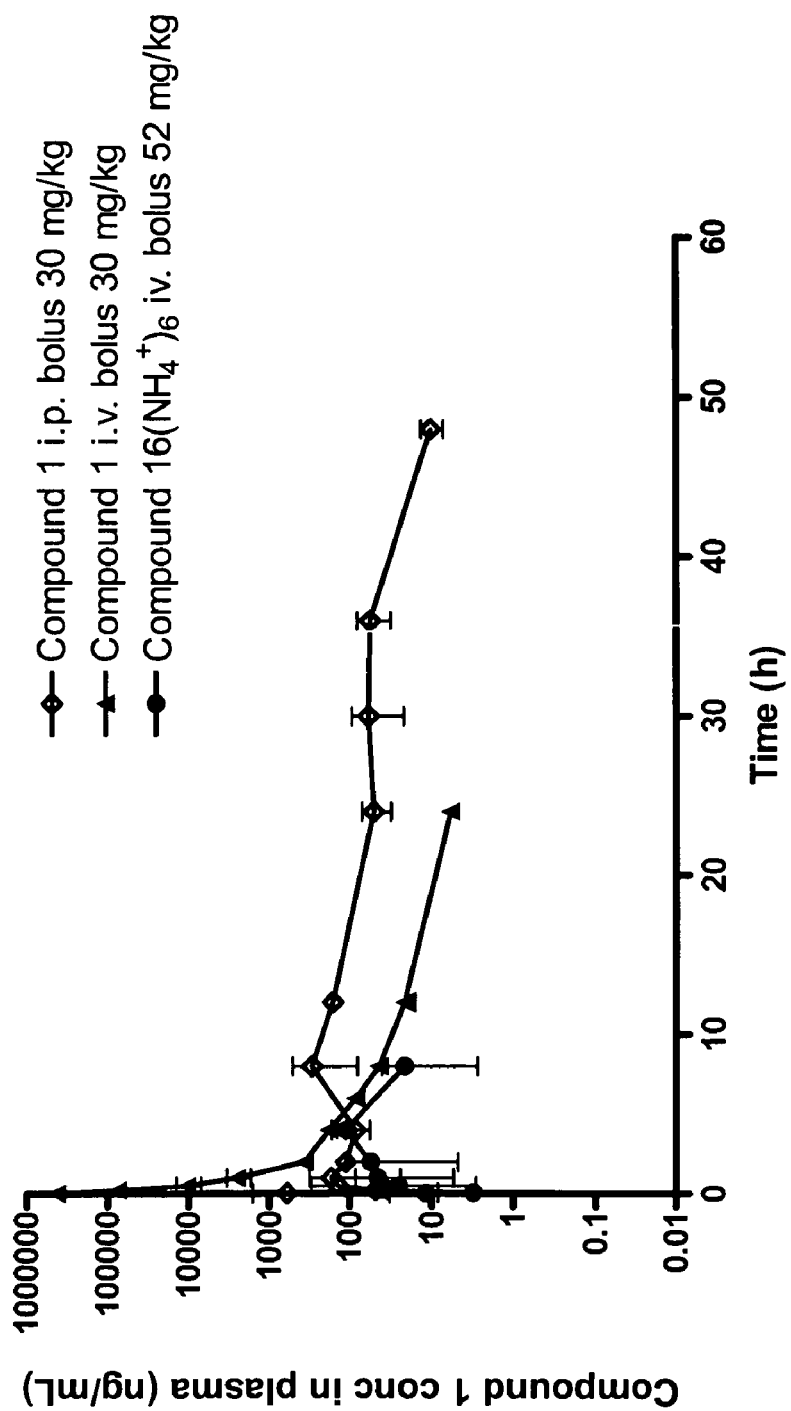
FIG. 4: shows mean (±SD) plasma concentrations of Compound 1, following bolus injection of Compound 1 (30 mg/kg, i.v. or i.p.) or Compound 16-hexaammonium (52 mg/kg, i.v.) in rats.

The results were compared to the PK studies of Compound 1 in rats and are presented in FIGS. 3 and 4. Compound 16-hexaammonium demonstrated conversion into Compound 1 following its i.v. injection. Although the AUC (area under the drug concentration-time curve) of Compound 1 generated from Compound 16-hexasodium (686 ng*h/mL) in the 8 hours of this study was more than 6 fold less than that obtained over the same period from a bolus i.v. injection of an equimolar amount of Compound 1 (70219 ng*h/mL) itself, most of that differential was obtained in the initial high level seen for the parent drug. Within 4 hours the blood levels of drug obtained from the prodrug were 62% those obtained from injection of the drug itself and this ratio was maintained at 8 hours.

(b) Compound 16-hexasodium

Figure 5:
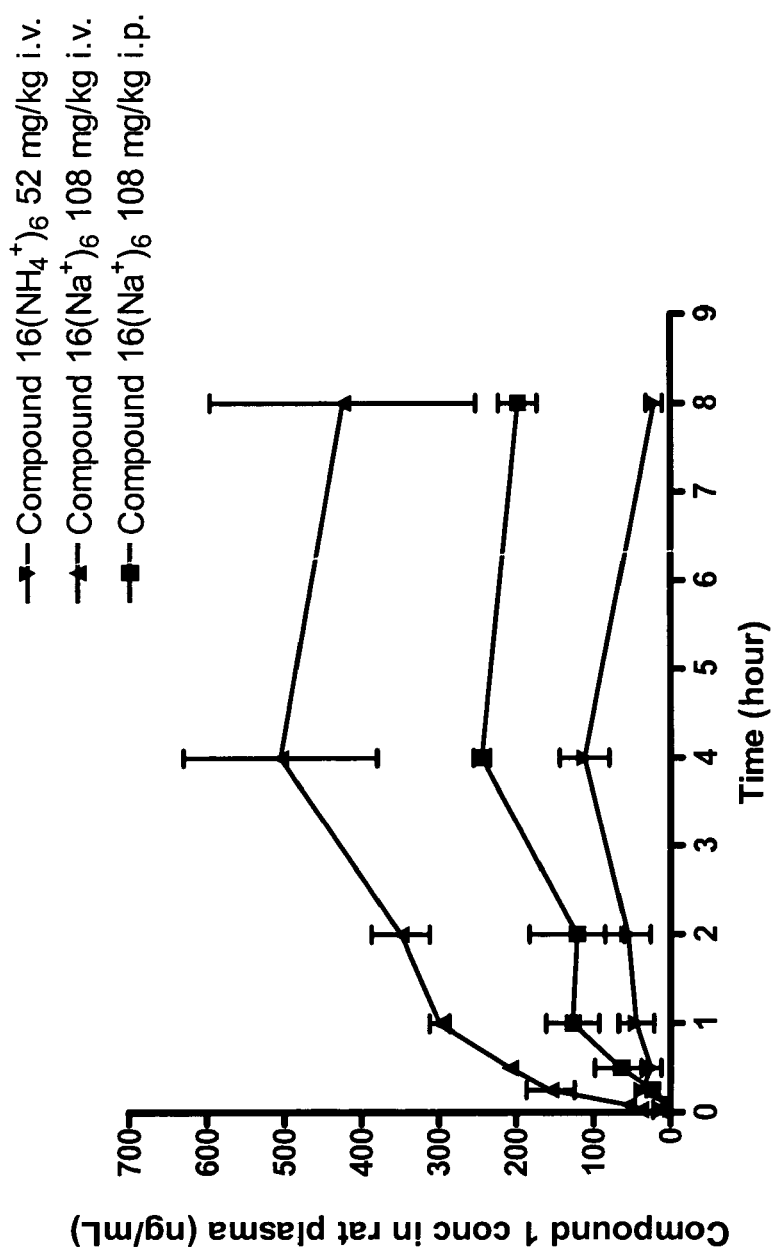
FIG. 5: shows mean (±SD) plasma concentrations of Compound 1, following bolus injection of Compound 16-hexammonium (52 mg/kg, i.v.) or Compound 16-hexasodium (108 mg/kg, i.v. or i.p.) in rats.

Compound 16-hexasodium was dissolved in 0.9% saline at a final concentration of 21.6 mg/mL. Compound 16-hexasodium was administered intravenously (i.v.) and intraperitonealy (i.p.) to the assigned animals at a dose of 108 mg/kg (volume of 5 mL/kg) (2 subsets of 3 rats each, for each administration route). This corresponds to 60 mg/kg of Compound 1 per dose. Blood was collected, centrifuged and analyzed as above. The results were compared to the PK studies done with Compound 16-hexaammonium and are presented in FIG. 5. Compound 16-hexasodium demonstrated conversion into Compound 1 following its i.v. injection.

Figure 6:
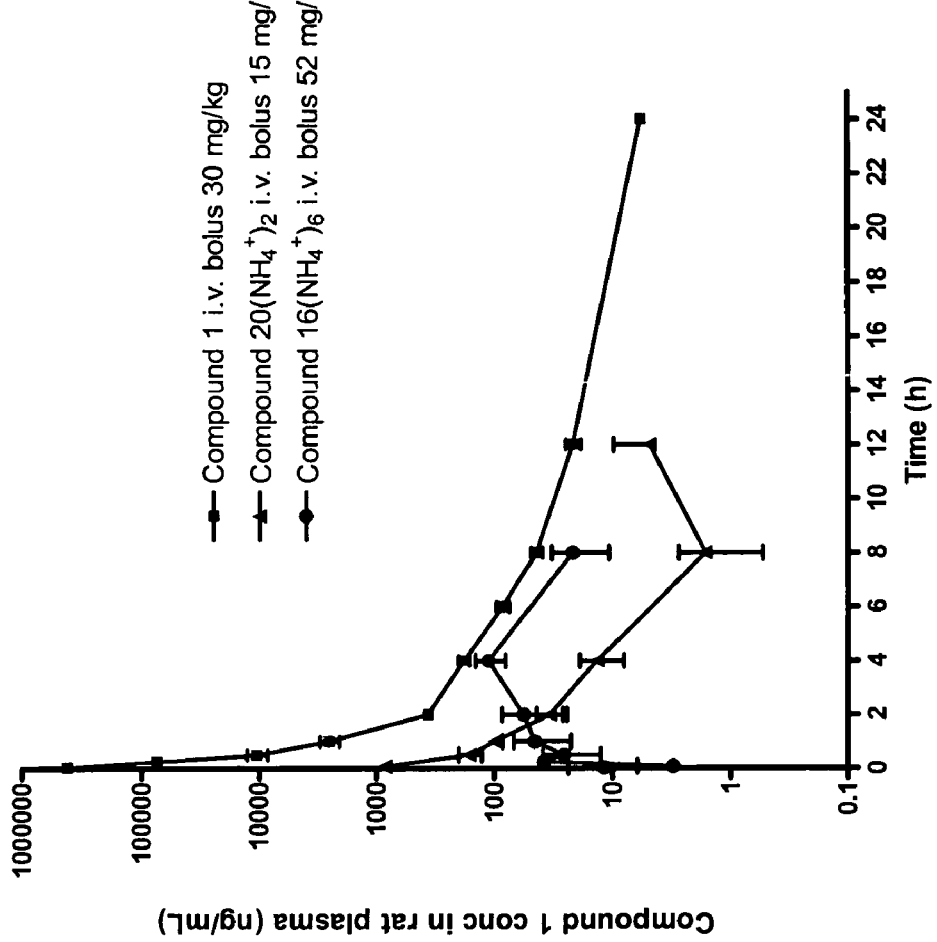
FIG. 6: shows mean (±SD) plasma concentrations of Compound 1, following bolus intravenous injection of Compound 1 (30 mg/kg), Compound 20-diammonium (15 mg/kg) or Compound 16-hexaammonium (52 mg/kg) in rats.

The i.p./i.v. AUC ratio is 44%, which corresponds to the maximum bioavailability of Compound 1 that could theoretically be obtained following oral administration of Compound 16-hexasodium (c) Compound 20-diammonium Compound 20-diammonium was dissolved in sterile water at a final concentration of 7 mg/mL for a target dose of 35 mg/kg (volume of 5 mL/kg), corresponding to 30 mg/kg. The dosing formulation was filtered on a 0.2-micron filter, leaving 44% percent of the original concentration as determined by LC/UV (294 nm) Compound 20-diammonium was administered intravenously (iv) to the assigned animals at a concentration of 3.14 mg/mL, and a dose of 15 mg/kg (volume of 5 mL/kg) (2 subsets of 3 rats each), corresponding to 13 mg/kg of Compound 1 per dose. Blood was collected, centrifuged and analyzed as above. The results were compared to the PK studies done with Compound 1 (30 mg/kg) and Compound 16-hexaammonium (52 mg/kg) and are presented in FIG. 6.

The AUC of Compound 1 generated from the administration of Compound 20-diaamonium was 30 to 100-fold lower than Compound 1, keeping in mind that the dose of Compound 20-diammonium was equivalent to 44% that of Compound 1. Compound 20-diammonium was shown to convert to Compound 1 in vivo in rats when administered intravenously. The rate of conversion observed for Compound 20-diammonium was higher than the rate of conversion for Compound 16-hexaammonium.

All patents, patent applications, and published references cited herein are hereby incorporated by reference in their entirety. While this invention has been particularly shown and described with references to preferred embodiments thereof, it will be understood by those skilled in the art that various changes in form and details may be made therein without departing from the scope of the invention encompassed by the appended claims.

The invention claimed is:

1. A compound of Formula I or a pharmaceutically acceptable salt thereof:

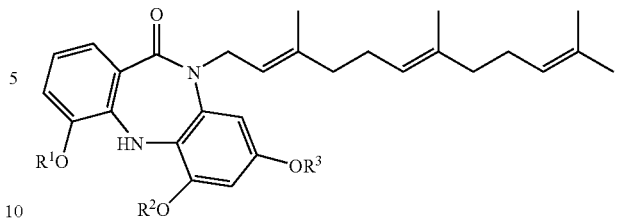

Formula I wherein,
$R^1$ $R^2$ and $R^3$ are each independently selected from the group consisting of H and a phosphate of formula II:

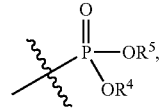

formula II wherein at least one of $R^{1,}$ $R^{2,}$ or $R^3$ is a phosphate of formula II;

$R^4$ and $R^5$ are each independently selected from the group consisting of H, $C_{1-10}$alkyl, $C_{2-10}$alkenyl, $C_{2-10}$alkynyl, $C_{6-10}$aryl, a 5-10 member heteroaryl, $C_{3-10}$cycloalkyl, and a 3-10 member heterocycloalkyl;

wherein, when either or both of $R^4$ and $R^5$ comprises an alkyl, alkenyl, alkynyl, aryl, heteroaryl, cycloalkyl, or heterocycloalkyl group, then said alkyl, alkenyl, alkynyl, aryl, heteroaryl, cycloalkyl, or heterocycloalkyl group is optionally substituted with one or more substituents selected from the group consisting of acyl, amino, acylamino, acyloxy, carboalkoxy, carboxy, carboxyamido, cyano, halo, hydroxyl, nitro, thiol, $C_{1-6}$alkyl, $C_{2-7}$alkenyl, $C_{2-7}$alkynyl, $C_{3-10}$cycloalkyl, a 3-10 member heterocycloalkyl, $C_{6-10}$aryl, a 5-10 member heteroaryl, alkoxy, aryloxy, sulfinyl, sulfonyl, oxo, guanidino and formyl.

2. A compound of Formula I or a pharmaceutically acceptable salt thereof:

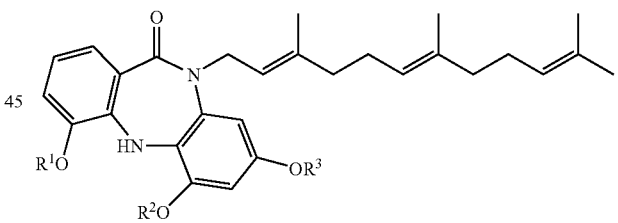

Formula I wherein,
$R^1$ $R^2$ and $R^3$ are each independently selected from the group consisting of H and a phosphate of formula II:

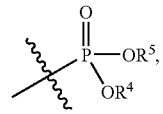

formula II wherein at least one of $R^{1,}$ $R^{2,}$ or $R^3$ is a phosphate of formula II;

$R^4$ and $R^5$ are each independently selected from the group consisting of H, $C_{1-10}$alkyl, $C_{2-10}$alkenyl, $C_{2-10}$alkynyl, $C_{6-10}$aryl, a 5-10 member heteroaryl, $C_{3-10}$cycloalkyl, and a 3-10 member heterocycloalkyl;

wherein at least one of $R^4$ and $R^5$ is H in at least one phosphate of formula II;

wherein, when either or both of $R^4$ and $R^5$ comprises an alkyl, alkenyl, alkynyl, aryl, heteroaryl, cycloalkyl, or heterocycloalkyl group, then said alkyl, alkenyl, alkynyl, aryl, heteroaryl, cycloalkyl, or heterocycloalkyl group is optionally substituted with one or more substituents selected from the group consisting of acyl, amino, acylamino, acyloxy, carboalkoxy, carboxy, carboxyamido, cyano, halo, hydroxyl, nitro, thiol, $C_{1-6}$alkyl, $C_{2-7}$alkenyl, $C_{2-7}$alkynyl, $C_{3-10}$cycloalkyl, a 3-10 member heterocycloalkyl, $C_{6-10}$aryl, a 5-10 member heteroaryl, alkoxy, aryloxy, sulfinyl, sulfonyl, oxo, guanidino and formyl.

3. The compound of claim 1 or 2, wherein $R^1$ is H, or a pharmaceutically acceptable salt of a compound of claim 1 or 2 wherein $R^1$ is H.

4. The compound of claim 1 or 2, wherein $R^2$ is H, or a pharmaceutically acceptable salt of a compound of claim 1 or 2 wherein $R^2$ is H.

5. The compound of claim 1 or 2, wherein $R^3$ is H, or a pharmaceutically acceptable salt f a compound of claim 1 or 2 wherein $R^3$ is H.

6. The compound of claim 1 or 2, wherein $R^1$ and $R^2$ are each H, or a pharmaceutically acceptable salt of a compound of claim 1 or 2 wherein $R^1$ and $R^2$ are each H.

7. The compound of claim 1 or 2, wherein $R^1$ and $R^3$ are each H, or a pharmaceutically acceptable salt of a compound of claim 1 or 2 wherein $R^1$ and $R^3$ are each H.

8. The compound of claim 1 or 2, wherein $R^2$ and $R^3$ are each H, or a pharmaceutically acceptable salt of a compound of claim 1 or 2 wherein $R^2$ and $R^3$ are each H.

9. The compound of claim 1 or 2, wherein $R^1$, $R^2$ and $R^3$ are each a phosphate of formula II, or a pharmaceutically acceptable salt of a compound of claim 1 or 2 wherein $R^1$, $R^2$ and $R^3$ are each a phosphate of formula II.

10. A compound selected from the group consisting of Compounds 2 to 22 or a pharmaceutically acceptable salt of any one thereof:

Compound 2

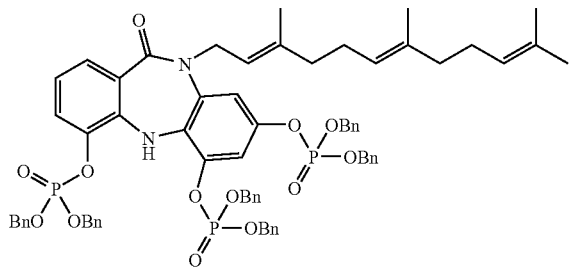

Compound 3

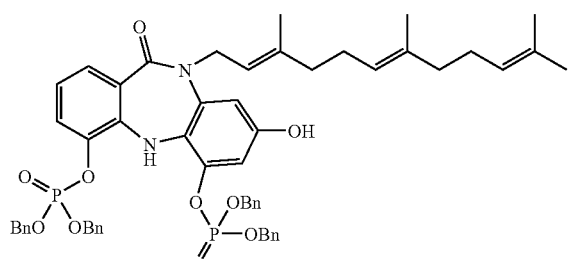

-continued

Compound 4

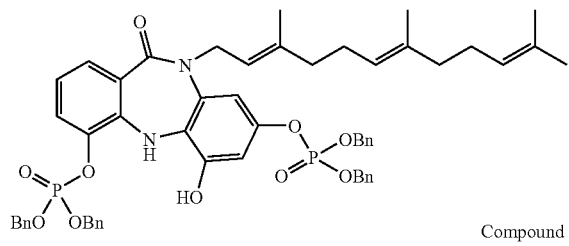

Compound 5

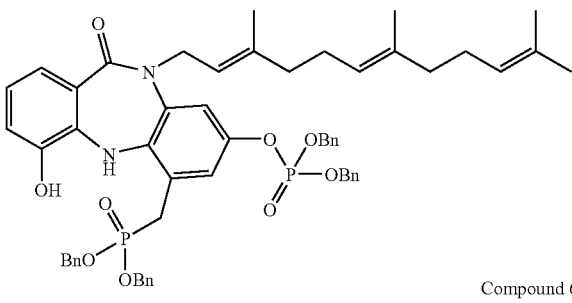

Compound 6

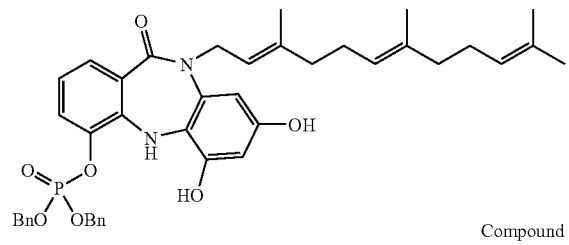

Compound 7

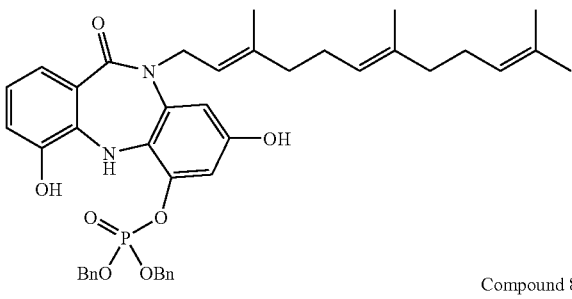

Compound 8

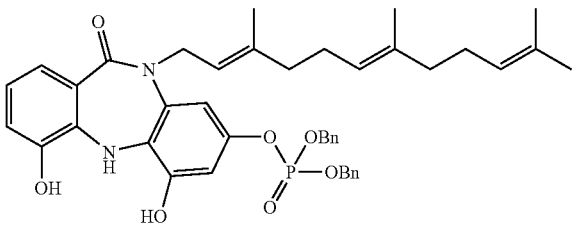

Compound 9

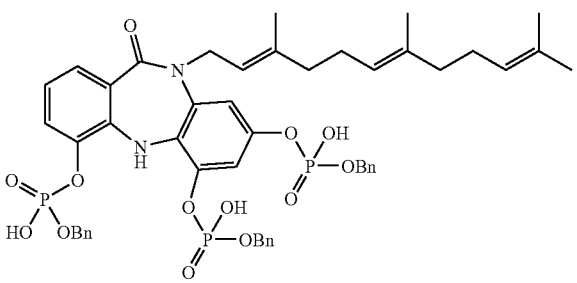

Compound 10
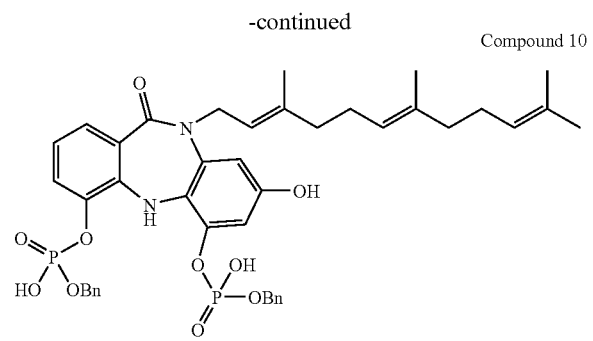
Compound 11
Compound 12
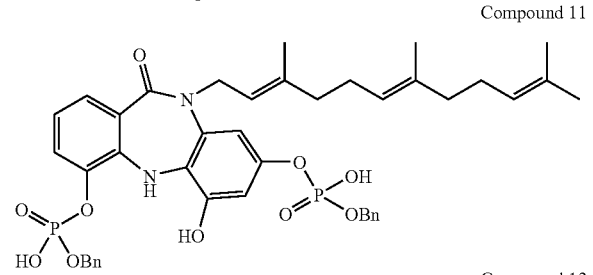
Compound 13
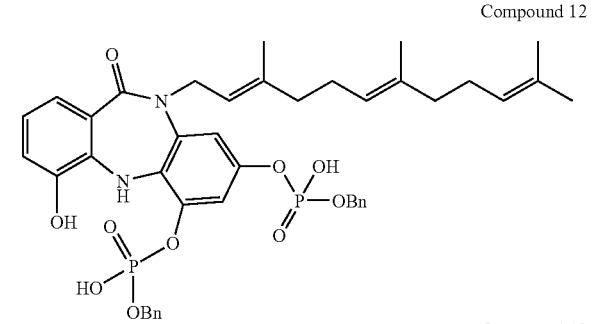
Compound 14
Compound 15
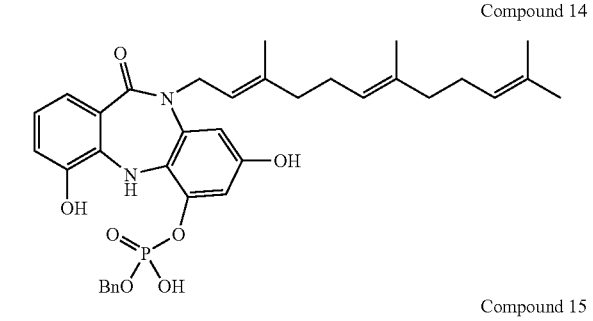
Compound 16
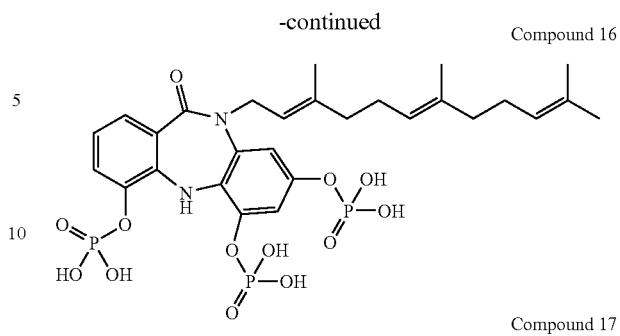
Compound 17
Compound 18
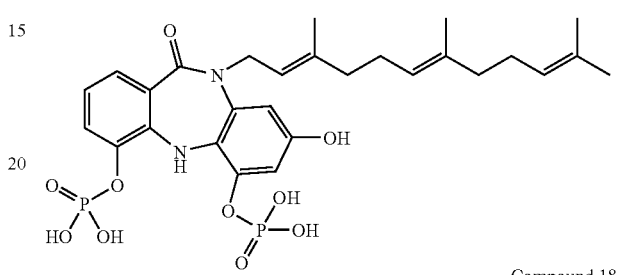
Compound 19
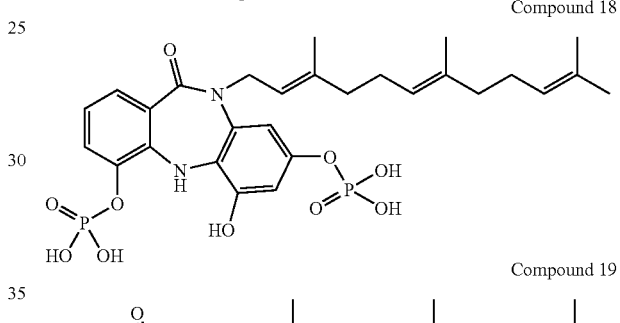
Compound 20
Compound 21
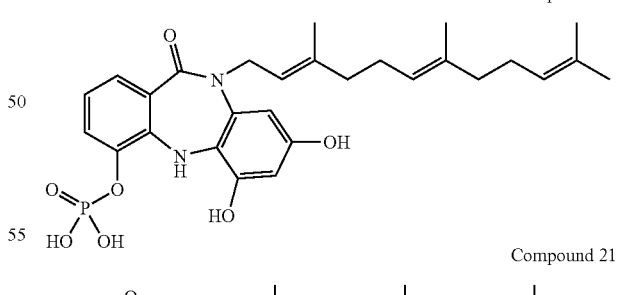
, and Compound 22

[Structure of Compound 22]

11. A method of producing a compound of any one of claims 1, 2 and 10, comprising
(a) phosphorylating Compound 1 to produce a compound of any one of claims 1, 2 and 10; and Compound 1

[Structure of Compound 1]

(b) isolating or purifying the compound produced in (a).

12. A method of producing a compound of any one of claims 1, 2 and 10, comprising
(a) protecting one or two reactive groups of Compound 1 to form a protected compound, Compound 1

[Structure of Compound 1]

(b) phosphorylating the protected compound of (a) to produce a protected phosphate ester any one of claim 1, 2 and 10; and
(c) deprotecting the protected phosphate ester of (b).

13. A method of producing a salt of a phosphate ester of claim 2, comprising:
(a) phosphorylating Compound 1 to produce a phosphate ester of claim 2;

Compound 1

[Structure of Compound 1]

(b) adding a base to remove a proton from $R^4$ or $R^5$ of the phosphate ester of (a) to produce a salt of a phosphate ester of claim 2; and (c) isolating or purifying the salt of said phosphate ester of claim 2 of (b).

14. A pharmaceutical composition comprising a compound of any one of claims 1, 2 and 10, and a pharmaceutically acceptable carrier.

15. A method of treating a mammal having a solid neoplasm or a hematopoietic neoplasm, said method comprising administering a therapeutically effective amount of a compound of any one of claims 1, 2, and 10 to a mammal in need of such treatment, thereby treating a mammal having a solid neoplasm or a hematopoietic neoplasm, wherein the solid neoplasm is selected from the group consisting of pancreatic cancer, prostate cancer, colorectal cancer, lung cancer, central nervous system cancer, ovarian cancer, melanoma, breast cancer, renal cancer and liver cancer, and wherein said hematopoietic neoplasm is leukemia or lymphoma.

16. The method of claim 15, wherein said mammal is a human.

17. The method of claim 15 wherein said method is a method of treating a mammal having a central nervous system cancer.

18. A method of inhibiting the growth or proliferation of a neoplastic cell, comprising contacting a neoplastic cell with a compound of any one of claims 1, 2, and 10, in an amount sufficient to inhibit growth or proliferation of said cell, thereby inhibiting the growth or proliferation of a neoplastic cell, wherein the neoplastic cell is a neoplastic cell of a neoplastic disorder selected from the group consisting of leukemia, hepatocellular cancer, sarcoma, vascular endothelial cancer, breast cancer, central nervous system cancer, prostate cancer, lung cancer, bronchus cancer, larynx cancer, esophagus cancer, colon cancer, colorectal cancer, gastro-intestinal cancer, melanoma, ovarian cancer, endometrial cancer, renal cancer, bladder cancer, liver cancer, endocrine cancer, and pancreatic cancer.

19. The method of claim 18, wherein said contacting occurs in vitro, in vivo or ex vivo.

20. The method of claim 18, wherein said cell is a human cell.

21. A method of treating a mammal having a solid neoplasm or a hematopoietic neoplasm, said method comprising administering a therapeutically effective amount of a pharmaceutical composition of claim 14 to a mammal in need of such treatment, thereby treating a mammal having a solid neoplasm or a hematopoietic neoplasm, wherein the solid neoplasm is selected from the group consisting of pancreatic cancer, prostate cancer, colorectal cancer, lung cancer, central nervous system cancer, ovarian cancer, melanoma, breast cancer, renal cancer and liver cancer, and wherein said hematopoietic neoplasm is leukemia or lymphoma.

22. The method of claim 21, wherein said mammal is a human.

* * * * *